(12) United States Patent
Birenbaum et al.

(10) Patent No.: US 11,950,950 B2
(45) Date of Patent: Apr. 9, 2024

(54) ZOOM DETECTION AND FLUOROSCOPE MOVEMENT DETECTION FOR TARGET OVERLAY

(71) Applicant: Covidien LP, Mansfield, MA (US)

(72) Inventors: Ariel Birenbaum, Raanana (IL); Oren P. Weingarten, Hod-Hasharon (IL); Irina Shevlev, Ashdod (IL); Guy Alexandroni, Yehud-Monosson (IL)

(73) Assignee: Covidien LP, Mansfield, MA (US)

( * ) Notice: Subject to any disclaimer, the term of this patent is extended or adjusted under 35 U.S.C. 154(b) by 289 days.

(21) Appl. No.: 17/350,922

(22) Filed: Jun. 17, 2021

(65) Prior Publication Data
US 2022/0022840 A1 Jan. 27, 2022

Related U.S. Application Data

(60) Provisional application No. 63/056,032, filed on Jul. 24, 2020.

(51) Int. Cl.
| | |
|---|---|
| *A61B 6/00* | (2006.01) |
| *A61B 90/00* | (2016.01) |
| *G06T 7/246* | (2017.01) |
| *G06T 7/73* | (2017.01) |

(52) U.S. Cl.
CPC ............ *A61B 6/547* (2013.01); *A61B 6/487* (2013.01); *A61B 90/39* (2016.02); *G06T 7/248* (2017.01); *G06T 7/74* (2017.01); *A61B 2090/3966* (2016.02); *G06T 2207/10121* (2013.01); *G06T 2207/30204* (2013.01)

(58) Field of Classification Search
CPC . A61B 6/487; A61B 90/39; A61B 2090/3966; G06T 7/70; G06T 2207/10121; G06T 2207/30204
See application file for complete search history.

(56) References Cited

U.S. PATENT DOCUMENTS

| | | |
|---|---|---|
| 8,335,359 B2 | 12/2012 | Fidrich et al. |
| 8,706,184 B2 | 4/2014 | Mohr et al. |
| 8,827,934 B2 | 9/2014 | Chopra et al. |

(Continued)

FOREIGN PATENT DOCUMENTS

| | | |
|---|---|---|
| BR | 0013237 A | 7/2003 |
| BR | 0116004 A | 6/2004 |

(Continued)

OTHER PUBLICATIONS

PCT Search Report and Written Opinion issued in PCT Application No. PCT/US2021/042878 dated Jan. 11, 2022.

(Continued)

*Primary Examiner* — Angela M Hoffa
*Assistant Examiner* — Younhee Choi
(74) *Attorney, Agent, or Firm* — Weber Rosselli & Cannon LLP

(57) ABSTRACT

Systems and methods for visualizing navigation of a medical device with respect to a target using a live fluoroscopic view. The methods include determining a level of zoom of a fluoroscope when acquiring a reference frame. The methods further include determining whether the live fluoroscopic images evidence movement of the fluoroscope relative to its position when capturing a reference frame.

12 Claims, 15 Drawing Sheets

(56) References Cited

U.S. PATENT DOCUMENTS

| | | |
|---|---|---|
| 9,918,659 B2 | 3/2018 | Chopra et al. |
| 10,373,719 B2 | 8/2019 | Soper et al. |
| 10,376,178 B2 | 8/2019 | Chopra |
| 10,405,753 B2 | 9/2019 | Sorger |
| 10,478,162 B2 | 11/2019 | Barbagli et al. |
| 10,480,926 B2 | 11/2019 | Froggatt et al. |
| 10,524,866 B2 | 1/2020 | Srinivasan et al. |
| 10,555,788 B2 | 2/2020 | Panescu et al. |
| 10,610,306 B2 | 4/2020 | Chopra |
| 10,638,953 B2 | 5/2020 | Duindam et al. |
| 10,674,970 B2 | 6/2020 | Averbuch et al. |
| 10,682,070 B2 | 6/2020 | Duindam |
| 10,706,543 B2 | 7/2020 | Donhowe et al. |
| 10,709,506 B2 | 7/2020 | Coste-Maniere et al. |
| 10,772,485 B2 | 9/2020 | Schlesinger et al. |
| 10,796,432 B2 | 10/2020 | Mintz et al. |
| 10,823,627 B2 | 11/2020 | Sanborn et al. |
| 10,827,913 B2 | 11/2020 | Ummalaneni et al. |
| 10,835,153 B2 | 11/2020 | Rafii-Tari et al. |
| 10,885,630 B2 | 1/2021 | Li et al. |
| 2003/0013972 A1 | 1/2003 | Makin |
| 2013/0303945 A1 | 11/2013 | Blumenkranz et al. |
| 2014/0035798 A1 | 2/2014 | Kawada et al. |
| 2014/0180064 A1* | 6/2014 | Nathaniel ............ G06T 7/0012 600/424 |
| 2015/0148690 A1 | 5/2015 | Chopra et al. |
| 2015/0265368 A1 | 9/2015 | Chopra et al. |
| 2016/0029989 A1* | 2/2016 | Nagae .................... A61B 6/469 378/42 |
| 2016/0157939 A1 | 6/2016 | Larkin et al. |
| 2016/0183841 A1 | 6/2016 | Duindam et al. |
| 2016/0192860 A1 | 7/2016 | Allenby et al. |
| 2016/0287344 A1 | 10/2016 | Donhowe et al. |
| 2017/0112576 A1 | 4/2017 | Coste-Maniere et al. |
| 2017/0209071 A1 | 7/2017 | Zhao et al. |
| 2017/0265952 A1 | 9/2017 | Donhowe et al. |
| 2017/0311844 A1 | 11/2017 | Zhao et al. |
| 2017/0319165 A1 | 11/2017 | Averbuch |
| 2018/0078318 A1 | 3/2018 | Barbagli et al. |
| 2018/0153621 A1 | 6/2018 | Duindam et al. |
| 2018/0235709 A1 | 8/2018 | Donhowe et al. |
| 2018/0240237 A1 | 8/2018 | Donhowe et al. |
| 2018/0256262 A1 | 9/2018 | Duindam et al. |
| 2018/0263706 A1 | 9/2018 | Averbuch |
| 2018/0279852 A1 | 10/2018 | Rafii-Tari et al. |
| 2018/0325419 A1 | 11/2018 | Zhao et al. |
| 2019/0000559 A1 | 1/2019 | Berman et al. |
| 2019/0000560 A1 | 1/2019 | Berman et al. |
| 2019/0008413 A1 | 1/2019 | Duindam et al. |
| 2019/0038365 A1 | 2/2019 | Soper et al. |
| 2019/0065209 A1 | 2/2019 | Mishra et al. |
| 2019/0110839 A1 | 4/2019 | Rafii-Tari et al. |
| 2019/0175062 A1 | 6/2019 | Rafii-Tari et al. |
| 2019/0183318 A1 | 6/2019 | Froggatt et al. |
| 2019/0183585 A1 | 6/2019 | Rafii-Tari et al. |
| 2019/0183587 A1 | 6/2019 | Rafii-Tari et al. |
| 2019/0192234 A1 | 6/2019 | Gadda et al. |
| 2019/0209016 A1 | 7/2019 | Herzlinger et al. |
| 2019/0209043 A1 | 7/2019 | Zhao et al. |
| 2019/0216548 A1 | 7/2019 | Ummalaneni |
| 2019/0239723 A1 | 8/2019 | Duindam et al. |
| 2019/0239831 A1 | 8/2019 | Chopra |
| 2019/0239837 A1 | 8/2019 | Barak et al. |
| 2019/0250050 A1 | 8/2019 | Sanborn et al. |
| 2019/0254649 A1 | 8/2019 | Walters et al. |
| 2019/0269470 A1 | 9/2019 | Barbagli et al. |
| 2019/0272634 A1 | 9/2019 | Li et al. |
| 2019/0298160 A1 | 10/2019 | Ummalaneni et al. |
| 2019/0298451 A1 | 10/2019 | Wong et al. |
| 2019/0320878 A1 | 10/2019 | Duindam et al. |
| 2019/0320937 A1 | 10/2019 | Duindam et al. |
| 2019/0336238 A1 | 11/2019 | Yu et al. |
| 2019/0343424 A1 | 11/2019 | Blumenkranz et al. |
| 2019/0350659 A1 | 11/2019 | Wang et al. |
| 2019/0365199 A1 | 12/2019 | Zhao et al. |
| 2019/0365479 A1 | 12/2019 | Rafii-Tari |
| 2019/0365486 A1 | 12/2019 | Srinivasan et al. |
| 2019/0380787 A1 | 12/2019 | Ye et al. |
| 2020/0000319 A1 | 1/2020 | Saadat et al. |
| 2020/0000526 A1 | 1/2020 | Zhao |
| 2020/0008655 A1 | 1/2020 | Schlesinger et al. |
| 2020/0030044 A1 | 1/2020 | Wang et al. |
| 2020/0030461 A1 | 1/2020 | Sorger |
| 2020/0038750 A1 | 2/2020 | Kojima |
| 2020/0043207 A1 | 2/2020 | Lo et al. |
| 2020/0046214 A1 | 2/2020 | Averbuch et al. |
| 2020/0046431 A1 | 2/2020 | Soper et al. |
| 2020/0046436 A1 | 2/2020 | Tzeisler et al. |
| 2020/0054399 A1 | 2/2020 | Duindam et al. |
| 2020/0060771 A1 | 2/2020 | Lo et al. |
| 2020/0069192 A1 | 3/2020 | Sanborn et al. |
| 2020/0077870 A1 | 3/2020 | Dicarlo et al. |
| 2020/0078095 A1 | 3/2020 | Chopra et al. |
| 2020/0078103 A1 | 3/2020 | Duindam et al. |
| 2020/0085514 A1 | 3/2020 | Blumenkranz |
| 2020/0109124 A1 | 4/2020 | Pomper et al. |
| 2020/0129045 A1 | 4/2020 | Prisco |
| 2020/0129239 A1 | 4/2020 | Bianchi et al. |
| 2020/0138515 A1 | 5/2020 | Wong |
| 2020/0155116 A1 | 5/2020 | Donhowe et al. |
| 2020/0170623 A1 | 6/2020 | Averbuch |
| 2020/0170720 A1 | 6/2020 | Ummalaneni |
| 2020/0179058 A1 | 6/2020 | Barbagli et al. |
| 2020/0188038 A1 | 6/2020 | Donhowe et al. |
| 2020/0205903 A1 | 7/2020 | Srinivasan et al. |
| 2020/0205904 A1 | 7/2020 | Chopra |
| 2020/0214664 A1 | 7/2020 | Zhao et al. |
| 2020/0229679 A1 | 7/2020 | Zhao et al. |
| 2020/0242767 A1 | 7/2020 | Zhao et al. |
| 2020/0275860 A1 | 9/2020 | Duindam |
| 2020/0297442 A1 | 9/2020 | Adebar et al. |
| 2020/0315554 A1 | 10/2020 | Averbuch et al. |
| 2020/0330795 A1 | 10/2020 | Sawant et al. |
| 2020/0352427 A1 | 11/2020 | Deyanov |
| 2020/0364865 A1 | 11/2020 | Donhowe et al. |

FOREIGN PATENT DOCUMENTS

| | | |
|---|---|---|
| CZ | 486540 | 9/2016 |
| CZ | 2709512 | 8/2017 |
| CZ | 2884879 | 1/2020 |
| EP | 3413830 A4 | 9/2019 |
| EP | 3478161 A4 | 2/2020 |
| EP | 3641686 A2 | 4/2020 |
| EP | 3644885 A1 | 5/2020 |
| EP | 3644886 A1 | 5/2020 |
| MX | PA03005028 A | 1/2004 |
| MX | 225663 B | 1/2005 |
| MX | 226292 | 2/2005 |
| MX | 246862 B | 6/2007 |
| MX | 265247 | 3/2009 |
| MX | 284569 B | 3/2011 |

OTHER PUBLICATIONS

Reaungamornrat Set Al: "An on-board surgical tracking and video augmentation system for c-arm image guidance", International Journal of Computer Assisted Radiology and Surgery; A Journal for Interdisciplinary Research, Development and Applications of Image Guided Diagnosis and Therapy, Springer, Berlin, DE, vol. 7, No. 5, Apr. 27, 2012 (Apr. 27, 2012), pp. 647-665.

* cited by examiner

ZOOM DETECTION AND FLUOROSCOPE MOVEMENT DETECTION FOR TARGET OVERLAY

CROSS-REFERENCE TO RELATED APPLICATION

The present application claims the benefit of and priority to U.S. Provisional Application Ser. No. 63/056,032, filed on Jul. 24, 2020, the entire contents of which are hereby incorporated by reference herein.

BACKGROUND

Technical Field

This disclosure relates to the field of visualizing the navigation of medical devices, such as biopsy or ablation tools, relative to targets, confirming the relative positions, and monitoring for movement of the fluoroscope.

Description of Related Art

There are several commonly applied medical methods, such as endoscopic procedures or minimally invasive procedures, for treating various maladies affecting organs including the liver, brain, heart, lungs, gall bladder, kidneys, and bones. Often, one or more imaging modalities, such as magnetic resonance imaging (Mill), ultrasound imaging, computed tomography (CT), or fluoroscopy are employed by clinicians to identify and navigate to areas of interest within a patient and ultimately a target for biopsy or treatment. In some procedures, pre-operative scans may be utilized for target identification and intraoperative guidance. However, real-time imaging may be required to obtain a more accurate and current image of the target area. Furthermore, real-time image data displaying the current location of a medical device with respect to the target and its surroundings may be needed to navigate the medical device to the target in a safe and accurate manner (e.g., without causing damage to other organs or tissue).

For example, an endoscopic approach has proven useful in navigating to areas of interest within a patient, and particularly so for areas within luminal networks of the body such as the lungs. To enable the endoscopic approach, and more particularly the bronchoscopic approach in the lungs, endobronchial navigation systems have been developed that use previously acquired Mill data or CT image data to generate a three-dimensional (3D) rendering, model, or volume of the particular body part such as the lungs.

The resulting volume generated from the MM scan or CT scan is then utilized to create a navigation plan to facilitate the advancement of a navigation catheter (or other suitable medical device) through a bronchoscope and a branch of the bronchus of a patient to an area of interest. A locating or tracking system, such as an electromagnetic (EM) tracking system, may be utilized in conjunction with, for example, CT data, to facilitate guidance of the navigation catheter through the branch of the bronchus to the area of interest. In certain instances, the navigation catheter may be positioned within one of the airways of the branched luminal networks adjacent to, or within, the area of interest to provide access for one or more medical instruments.

However, a 3D volume of a patient's lungs, generated from previously acquired scans, such as CT scans, may not provide a basis sufficient for accurate guiding of medical devices or instruments to a target during a navigation procedure. In some cases, the inaccuracy is caused by deformation of the patient's lungs during the procedure relative to the lungs at the time of the acquisition of the previously acquired CT data. This deformation (CT-to-Body divergence) may be caused by many different factors including, for example, changes in the body when transitioning from between a sedated state and a non-sedated state, the bronchoscope changing the patient's pose, the bronchoscope pushing the tissue, different lung volumes (e.g., the CT scans are acquired during inhale while navigation is performed during breathing), different beds, different days, etc.

Thus, another imaging modality is needed to visualize medical devices and targets in real-time and enhance the in-vivo navigation procedure. Furthermore, to accurately and safely navigate medical devices to a remote target, for example, for biopsy or treatment, both the medical device and the target should be visible in a guidance system.

SUMMARY

This disclosure is directed to systems and methods for visualizing intra-body navigation of a medical device relative to a target using a live 2D fluoroscopic view. In accordance with the disclosure, one aspect is directed to method of determining a level of zoom in a fluoroscopic image including capturing a fluoroscopic reference frame, calculating an interval between radio opaque markers in the reference frame, calculating an expected interval between radio opaque markers for all levels of zoom and identifying the expected interval that most closely matches calculated interval in the reference frame.

In aspects, the method may further include storing a height of a fluoroscope from which the fluoroscopic reference frame is captured compared to a location of the radio opaque markers.

In aspects, the method may further include storing an angle of the fluoroscope from which the fluoroscopic reference frame is captured compared to a location of the radio opaque markers.

In other aspects, the method may further include recalling the height of the fluoroscope.

In certain aspects, calculating the expected interval between radio opaque markers may include calculating the expected interval between the radio opaque markers at the recalled height of the fluoroscope at which the reference frame was captured.

In aspects, the method may further include applying a transform such that a location of a target can be accurately overlaid on a live fluoroscopic image.

In certain aspects, capturing the fluoroscopic reference frame may include capturing the fluoroscopic reference frame when a fluoroscope from which the fluoroscopic reference frame is captured is in an anteroposterior position.

In other aspects, capturing the fluoroscopic reference frame may include capturing the fluoroscopic reference frame through a sweep through about 30-60 degrees relative to an anteroposterior position.

Another aspect of the disclosure is directed to a method of detecting movement of a fluoroscope including capturing a reference frame, determining locations of radio opaque markers in the reference frame, creating a Gaussian mask, determining the locations of radio opaque markers in live fluoroscopic images, comparing the determined positions of the radio opaque markers in the live fluoroscopic images to the Gaussian mask, and determining whether the fluoroscope has moved relative to its position when the reference frame was captured.

In aspects, determining the locations of the radio opaque markers may include determining locations of the radio opaque markers in the reference frame using thresholding.

In other aspects, determining the locations of the radio opaque markers may include determining a two-dimensional position of the radio opaque markers in a coordinate system of the fluoroscope.

In certain aspects, creating a gaussian mask may include creating a Gaussian mask by defining an acceptable range of movement around the determined locations of the radio opaque markers.

In other aspects, the acceptable range of movement is an acceptable range of movement in both an X and a Y direction in the reference frame.

In certain aspects, determining whether the fluoroscope has moved may include determining whether the position of the radio opaque markers is outside of the Gaussian mask.

Yet a further aspect of the disclosure is directed to a method including acquiring a reference frame, determining a level of zoom in the reference frame, acquiring a position of a catheter, receiving a marked location of the catheter in the reference frame, generate a translation from the marked location and the detected position, acquire live fluoroscopic images; determining whether the fluoroscope has moved from the position at which the reference frame was acquired, and overlaying a target identified in prior fluoroscopic images on the live fluoroscopic images.

In aspects, acquiring the reference frame may include acquiring the reference frame through a sweep of the fluoroscope through about 30-60 degrees relative to an anteroposterior position.

In other aspects, determining the level of zoom may include calculating an interval between radio opaque markers in the reference frame, calculating an expected interval between the radio opaque markers for all levels of zoom, and identifying the expected interval that most closely matches the calculated interval in the reference frame.

In certain aspects, calculating the expected interval between radio opaque markers may include calculating the expected interval between the radio opaque markers at a recalled height and angle of the fluoroscope relative to a location of the radio opaque markers.

In other aspects, determining whether the fluoroscope has moved may include determining locations of radio opaque markers in the reference frame, creating a Gaussian mask, determining the locations of the radio opaque markers in live fluoroscopic images, comparing the determined positions of the radio opaque markers in the live fluoroscopic images to the Gaussian mask, and determining whether the fluoroscope has moved relative to its position when the reference frame was acquired.

In certain aspects, determining whether the fluoroscope has moved includes determining whether the position of the radio opaque markers is outside of the Gaussian mask.

BRIEF DESCRIPTION OF THE DRAWINGS

Various aspects and embodiments of the disclosure are described hereinbelow with references to the drawings, wherein.

DETAILED DESCRIPTION

Figure 1:
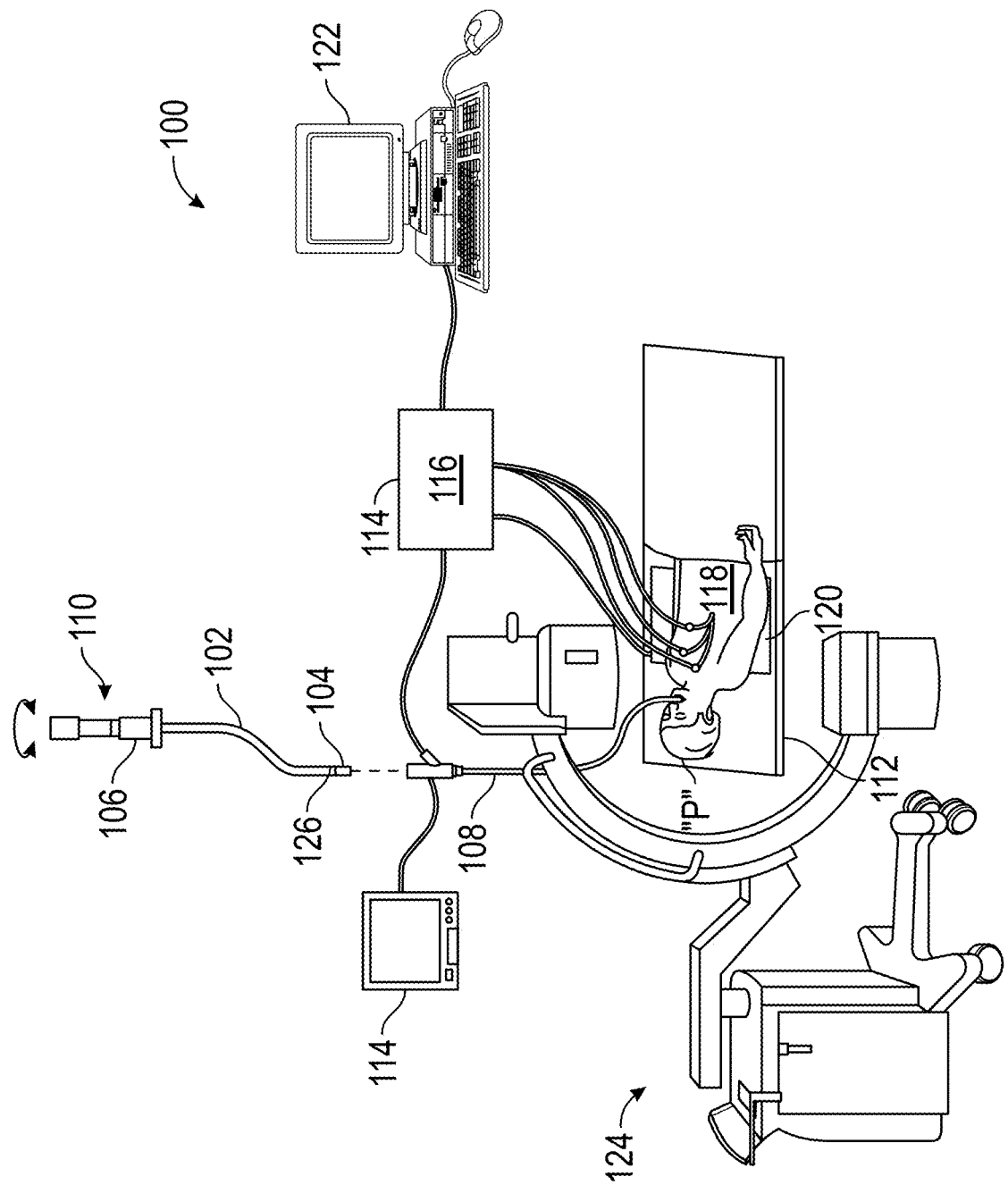
FIG. 1 is a schematic diagram of a system for navigating to soft-tissue targets via luminal networks in accordance with the disclosure.

A fluoroscopic imaging device may be used by a clinician, for example, to visualize the navigation of a medical device and confirm the placement of the medical device after it has been navigated to a desired location. However, although fluoroscopic images show highly dense objects, such as metal tools, bones, and large soft-tissue objects, e.g., the heart, the fluoroscopic images may not clearly show small soft-tissue objects of interest, such as lesions. Furthermore, the fluoroscopic images are two-dimensional projections. Therefore, an X-ray volumetric reconstruction is needed to enable identification of soft tissue objects and navigation of medical devices to those objects.

Several solutions exist that provide 3D volume reconstruction. One solution is a CT machine, which algorithmically combines multiple X-ray projections from known, calibrated X-ray source positions into a 3D volume, in which soft tissues are more visible. For example, a CT machine can be used with iterative scans during a procedure to provide guidance through the body until the tool or tools reach the target. This is a tedious procedure, as it requires several full CT scans, a dedicated CT room, and blind navigation between scans. In addition, each scan requires the staff to leave the room due to high levels of ionizing radiation and exposes the patient to the radiation. Another solution is a cone-beam CT machine. However, the cone-beam CT machine is expensive and, like the CT machine, only provides blind navigation between scans, requires multiple iterations for navigation, and requires the staff to leave the room. In some example embodiments, the systems and methods of this disclosure combine the benefits of CT machines and fluoroscopic imaging devices to help clinicians navigate medical devices to targets, including small soft-tissue objects.

In an electromagnetic navigation procedure, planning, registration, and navigation are performed to ensure that a medical device, e.g., a biopsy tool, follows a planned path to reach a target, e.g., a lesion, so that a biopsy or treatment of the target can be completed. Following the navigation phase, fluoroscopic images may be captured and utilized in a local registration process to reduce CT-to-body divergence. After the local registration process, the locatable guide may be removed from the extended working channel and a medical device, e.g., a biopsy tool, is introduced into the extended working channel and navigated to the target to perform the biopsy or treatment of the target, e.g., the lesion.

In navigating the medical device to the target, clinicians may use a live 2D fluoroscopic view to visualize the position of the medical device relative to the target. While the medical device may be clearly visible in the live fluoroscopic view, some targets, e.g., lesions, may not be visible in the live fluoroscopic view. And electromagnetic navigation cannot be used because some medical devices do not include sensors. Moreover, the user interfaces that are used to advance or navigate a medical device towards the target do not provide enough information regarding the medical device relative to the target, including when the medical device is near the target.

This disclosure features a user interface which overlays a 2D target marker, which corresponds to a three-dimensional model of a target identified in a CT scan, on the live 2D fluoroscopic view so that a clinician can visualize the position of the medical device tip relative to the target. Since the live fluoroscopic view with the target overlay is a two-dimensional view and does not necessarily show whether the medical device is above or below the target, the same user interface also includes a three-dimensional, medical device tip view of the 3D model of the target, which enables a clinician to confirm that the medical device is not above or below the target.

The user interface also provides a graphical indication of whether the medical device is aligned with the target in three dimensions. For example, when the medical device is aligned in three-dimensions with the target, the user interface shows the target overlay in a first color, e.g., green. On the other hand, when the medical device is not aligned with the target in three dimensions, the user interface shows the target overlay in a second color different from the first color, e.g., orange or red.

In accordance with aspects of the disclosure, the visualization of intra-body navigation of a medical device, e.g., a biopsy tool, towards a target, e.g., a lesion, may be a portion of a larger workflow of a navigation system, such as an electromagnetic navigation system. FIG. 1 is a perspective view of an exemplary system for facilitating navigation of a medical device, e.g., a biopsy tool, to a soft-tissue target via airways of the lungs. System 100 may be further configured to construct fluoroscopic based three-dimensional volumetric data of the target area from 2D fluoroscopic images. System 100 may be further configured to facilitate approach of a medical device to the target area by using Electromagnetic Navigation Bronchoscopy (ENB) and for determining the location of a medical device with respect to the target.

One aspect of the system 100 is a software component for reviewing of computed tomography (CT) image data that has been acquired separately from system 100. The review of the CT image data allows a user to identify one or more targets, plan a pathway to an identified target (planning phase), navigate a catheter 102 to the target (navigation phase) using a user interface, and confirming placement of a sensor 104 relative to the target. One such EMN system is the ELECTROMAGNETIC NAVIGATION BRONCHOSCOPY® system currently sold by Medtronic PLC. The target may be tissue of interest identified by review of the CT image data during the planning phase. Following navigation, a medical device, such as a biopsy tool or other tool, may be inserted into catheter 102 to obtain a tissue sample from the tissue located at, or proximate to, the target.

As shown in FIG. 1, catheter 102 is part of a catheter guide assembly 106. In practice, catheter 102 is inserted into a bronchoscope 108 for access to a luminal network of the patient P. Specifically, catheter 102 of catheter guide assembly 106 may be inserted into a working channel of bronchoscope 108 for navigation through a patient's luminal network. A locatable guide (LG) 110, including a sensor 104 is inserted into catheter 102 and locked into position such that sensor 104 extends a desired distance beyond the distal tip of catheter 102. The position and orientation of sensor 104 relative to the reference coordinate system, and thus the distal portion of catheter 102, within an electromagnetic field can be derived. Catheter guide assemblies 106 are currently marketed and sold by Medtronic PLC under the brand names SUPERDIMENSION® Procedure Kits, or EDGE™ Procedure Kits, and are contemplated as useable with the disclosure.

System 100 generally includes an operating table 112 configured to support a patient P, a bronchoscope 108 configured for insertion through patient P's mouth into patient P's airways; monitoring equipment 114 coupled to bronchoscope 108 (e.g., a video display, for displaying the video images received from the video imaging system of bronchoscope 108); a locating or tracking system 114 including a locating module 116, a plurality of reference sensors 18 and a transmitter mat 120 including a plurality of incorporated markers; and a computing device 122 including software and/or hardware used to facilitate identification of a target, pathway planning to the target, navigation of a medical device to the target, and/or confirmation and/or determination of placement of catheter 102, or a suitable device therethrough, relative to the target. Computing device 122 may be similar to workstation 1501 of FIG. 15 and may be configured to execute the methods of the disclosure including the method of FIGS. 10, 11, 13, and 14.

A fluoroscopic imaging device 124 capable of acquiring fluoroscopic or x-ray images or video of the patient P is also included in this particular aspect of system 100. The images, sequence of images, or video captured by fluoroscopic imaging device 124 may be stored within fluoroscopic imaging device 124 or transmitted to computing device 122 for storage, processing, and display. Additionally, fluoroscopic imaging device 124 may move relative to the patient P so that images may be acquired from different angles or perspectives relative to patient P to create a sequence of fluoroscopic images, such as a fluoroscopic video. The pose of fluoroscopic imaging device 124 relative to patient P and while capturing the images may be estimated via markers incorporated with the transmitter mat 120. The markers are positioned under patient P, between patient P and operating table 112 and between patient P and a radiation source or a sensing unit of fluoroscopic imaging device 124. The markers incorporated with the transmitter mat 120 may be two separate elements which may be coupled in a fixed manner or alternatively may be manufactured as a single unit. Fluoroscopic imaging device 124 may include a single imaging device or more than one imaging device.

Computing device 122 may be any suitable computing device including a processor and storage medium, wherein the processor is capable of executing instructions stored on the storage medium. Computing device 122 may further include a database configured to store patient data, CT data sets including CT images, fluoroscopic data sets including fluoroscopic images and video, fluoroscopic 3D reconstruction, navigation plans, and any other such data. Although not explicitly illustrated, computing device 122 may include inputs, or may otherwise be configured to receive, CT data sets, fluoroscopic images/video and other data described herein. Additionally, computing device 122 includes a display configured to display graphical user interfaces. Computing device 122 may be connected to one or more networks through which one or more databases may be accessed.

With respect to the planning phase, computing device 122 utilizes previously acquired CT image data for generating and viewing a three-dimensional model or rendering of patient P's airways, enables the identification of a target on the three-dimensional model (automatically, semi-automatically, or manually), and allows for determining a pathway through patient P's airways to tissue located at and around the target. More specifically, CT images acquired from previous CT scans are processed and assembled into a three-dimensional CT volume, which is then utilized to generate a three-dimensional model of patient P's airways. The three-dimensional model may be displayed on a display associated with computing device 122, or in any other suitable fashion. Using computing device 122, various views of the three-dimensional model or enhanced two-dimensional images generated from the three-dimensional model are presented. The enhanced two-dimensional images may possess some three-dimensional capabilities because they are generated from three-dimensional data. The three-dimensional model may be manipulated to facilitate identification of target on the three-dimensional model or two-dimensional images, and selection of a suitable pathway through patient P's airways to access tissue located at the target can be made. Once selected, the pathway plan, three-dimensional model, and images derived therefrom, can be saved and exported to a navigation system for use during the navigation phase(s). One such planning software is the ILLUMISITE® planning suite currently sold by Medtronic PLC.

With respect to the navigation phase, a six degrees-of-freedom electromagnetic locating or tracking system 114, or other suitable system for determining location, is utilized for performing registration of the images and the pathway for navigation, although other configurations are also contemplated. Tracking system 114 includes the tracking module 116, a plurality of reference sensors 118, and the transmitter mat 120 (including the markers). Tracking system 114 is configured for use with a locatable guide 110 and particularly sensor 104. As described above, locatable guide 110 and sensor 104 are configured for insertion through catheter 102 into patient P's airways (either with or without bronchoscope 108) and are selectively lockable relative to one another via a locking mechanism.

Transmitter mat 120 is positioned beneath patient P. Transmitter mat 120 generates an electromagnetic field around at least a portion of the patient P within which the position of a plurality of reference sensors 118 and the sensor 104 can be determined with use of a tracking module 116. A second electromagnetic sensor 126 may also be incorporated into the end of the catheter 102. The second electromagnetic sensor 126 may be a five degree-of-freedom sensor or a six degree-of-freedom sensor. One or more of reference sensors 118 are attached to the chest of the patient P. The six degrees of freedom coordinates of reference sensors 118 are sent to computing device 122 (which includes the appropriate software) where they are used to calculate a patient coordinate frame of reference. Registration is generally performed to coordinate locations of the three-dimensional model and two-dimensional images from the planning phase, with the patient P's airways as observed through the bronchoscope 108, and allow for the navigation phase to be undertaken with precise knowledge of the location of the sensor 104, even in portions of the airway where the bronchoscope 108 cannot reach.

Registration of the patient P's location on the transmitter mat 120 may be performed by moving sensor 104 through the airways of the patient P. More specifically, data pertaining to locations of sensor 104, while locatable guide 110 is moving through the airways, is recorded using transmitter mat 120, reference sensors 118, and tracking system 114. A shape resulting from this location data is compared to an interior geometry of passages of the three-dimensional model generated in the planning phase, and a location correlation between the shape and the three-dimensional model based on the comparison is determined, e.g., utilizing the software on computing device 122. In addition, the software identifies non-tissue space (e.g., air filled cavities) in the three-dimensional model. The software aligns, or registers, an image representing a location of sensor 104 with the three-dimensional model and/or two-dimensional images generated from the three-dimension model, which are based on the recorded location data and an assumption that locatable guide 110 remains located in non-tissue space in patient P's airways. Alternatively, a manual registration technique may be employed by navigating the bronchoscope 108 with the sensor 104 to pre-specified locations in the lungs of the patient P, and manually correlating the images from the bronchoscope to the model data of the three-dimensional model.

Though described herein with respect to EMN systems using EM sensors, the instant disclosure is not so limited and may be used in conjunction with flexible sensor, ultrasonic sensors, or without sensors. Additionally, the methods described herein may be used in conjunction with robotic systems such that robotic actuators drive the catheter 102 or bronchoscope 108 proximate the target.

Following registration of the patient P to the image data and pathway plan, a user interface is displayed in the navigation software which sets for the pathway that the clinician is to follow to reach the target. Once catheter 102 has been successfully navigated proximate the target as depicted on the user interface, the locatable guide 110 may be unlocked from catheter 102 and removed, leaving catheter 102 in place as a guide channel for guiding medical devices including without limitation, optical systems, ultrasound probes, marker placement tools, biopsy tools, ablation tools (i.e., microwave ablation devices), laser probes, cryogenic probes, sensor probes, and aspirating needles to the target. A medical device may be then inserted through catheter 102 and navigated to the target or to a specific area adjacent to the target.

Prior to inserting the medical device through the catheter 102, a local registration process may be performed for each target to reduce the CT-to-body divergence. In a capture phase of the local registration process, a sequence of fluoroscopic images may be captured and acquired via fluoroscopic imaging device 124, optionally by a user and according to directions displayed via computing device 122. A fluoroscopic 3D reconstruction may be then generated via computing device 122. The generation of the fluoroscopic 3D reconstruction is based on the sequence of fluoroscopic images and the projections of structure of markers incorporated with transmitter mat 120 on the sequence of images. One or more slices of the 3D reconstruction may be then generated based on the pre-operative CT scan and via computing device 122. The one or more slices of the 3D reconstruction and the fluoroscopic 3D reconstruction may be then displayed to the user on a display via computing device 122, optionally simultaneously. The slices of 3D reconstruction may be presented on the user interface in a scrollable format where the user is able to scroll through the slices in series.

In a marking phase of the local registration process, the clinician may be directed to identify and mark the target while using the slices of the 3D reconstruction as a reference. The user may also be directed to identify and mark the navigation catheter tip in the sequence of fluoroscopic 2D images. An offset between the location of the target and the navigation catheter tip may be then determined or calculated via computer device 122. The offset may be then utilized, via computing device 122, to correct the location and/or orientation of the navigation catheter on the display (e.g., in the peripheral navigation screen which may be viewed by selecting the "Peripheral Navigation" tab 401 illustrated in FIG. 4) with respect to the target and/or correct the registration between the three-dimensional model and tracking system 114 in the area of the target and/or generate a local registration between the three-dimensional model and the fluoroscopic 3D reconstruction in the target area.

Figure 2:
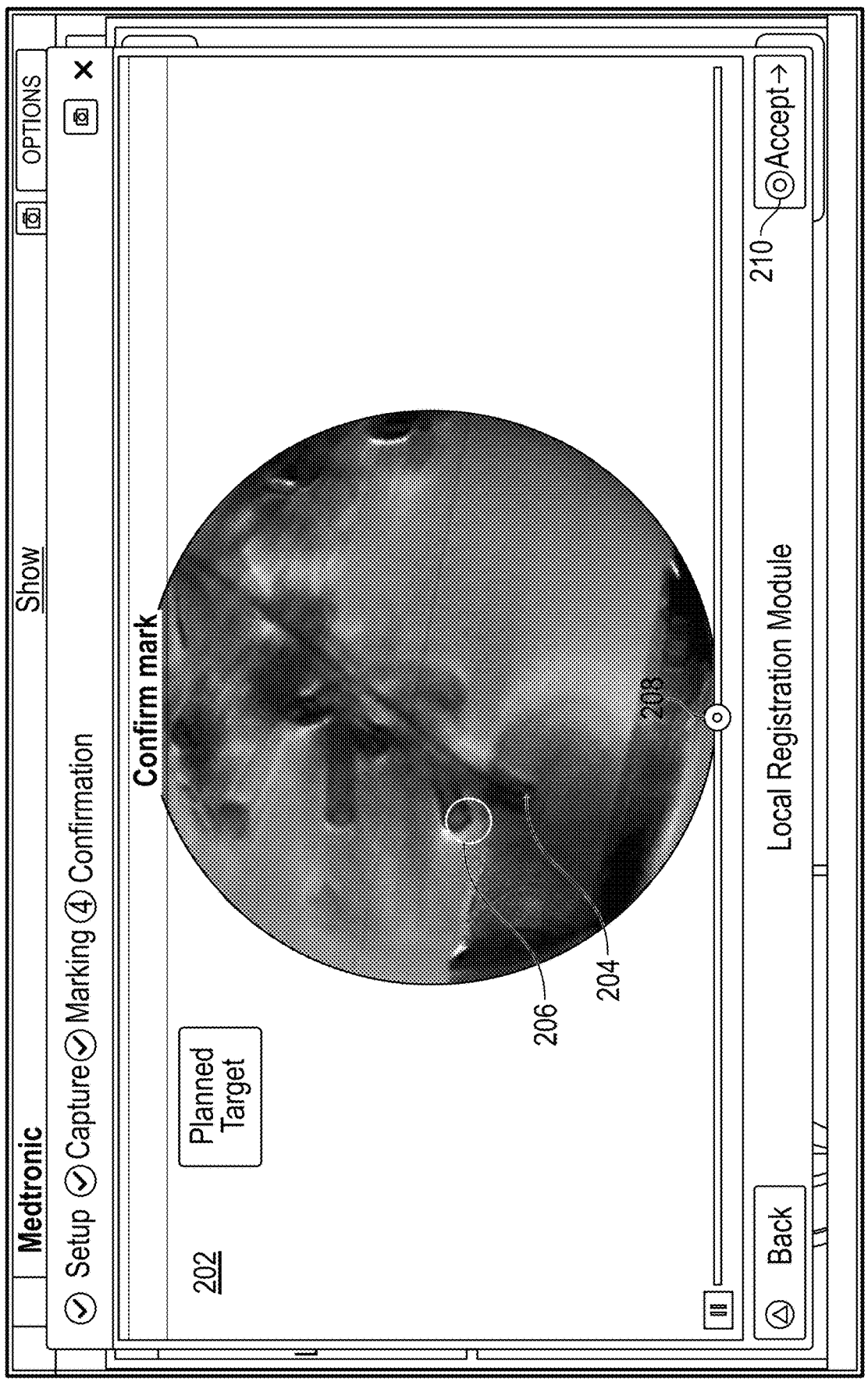
FIG. 2 is a screen shot of an example user interface for confirming local registration in accordance with the disclosure.

In a confirmation phase of the local registration process, a fluoroscopic 3D reconstruction is displayed in a confirmation screen 202, which is illustrated in FIG. 2. The confirmation screen 202 includes a slider 208 that may be selected and moved by the user to review a video loop of the fluoroscopic 3D reconstruction, which shows the marked target and navigation catheter tip from different perspectives. After confirming that there are marks on the target and navigation catheter tip throughout the video, the clinician may select the "Accept" button 210, at which point the local registration process ends and the position of the navigation catheter is updated. The clinician may then use the navigation views in, for example, the peripheral navigation screen illustrated in FIG. 4 to fine tune the alignment of the navigation catheter to the target before beginning an endoscopic procedure.

After the local registration process, the clinician or robot may insert a medical device in the catheter 102 and advance the medical device towards the target. While advancing the medical device towards the target, the clinician may view a user interface screen which includes: (a) a 3D medical device tip view of a 3D model of a target based on pre-operative CT scans, and (b) a live 2D fluoroscopic view on which a target marker corresponding to the 3D model of the target is overlaid. This user interface screen allows the clinician to not only see the medical device in real-time, but also allows the clinician to see whether the medical device is aligned with the target. The user interface screen may also provide a graphical indication of whether the medical device is aligned in three-dimensions with the target. For example, when the medical device is aligned in three-dimensions with the target, the user interface shows the target overlay in a first color, e.g., green. On the other hand, when the medical device is not aligned with the target in three dimensions, the user interface shows the target overlay in a second color different from the first color, e.g., orange or red.

Figure 3:
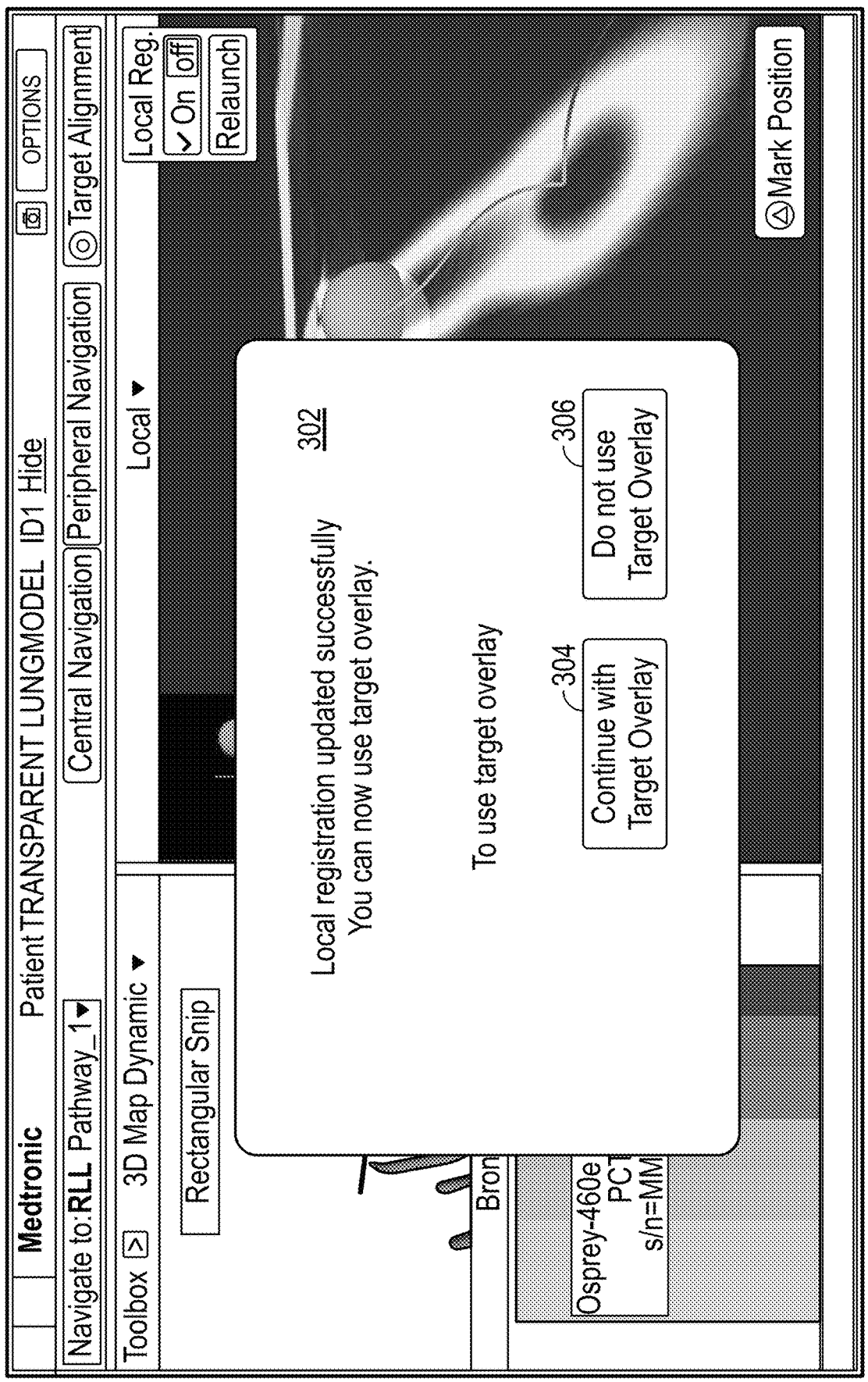
FIG. 3 is a screen shot of an example navigation user interface with a pop-up message inquiring about whether to continue with a target overlay feature in accordance with the disclosure.

FIG. 2 is a screen shot of a confirmation screen 202 of an example local registration user interface that appears during the confirmation phase of the local registration process. The confirmation screen 202 displays the navigation catheter tip mark 204 and the target mark 206, which were previously marked by the clinician during the marking phase of the local registration process. After the clinician selects the "Accept" button, the navigation user interface of FIG. 3 is displayed with a pop-up message 302. The pop-up message 302 may include buttons 304, 306, which enable the clinician to select whether to use the target overlay feature to guide navigation of a medical device, e.g., a biopsy tool, to the target. Specifically, the clinician may select button 304 to continue with the target overlay feature or the clinician may select button 306 to continue without using the target overlay feature.

Figure 4:
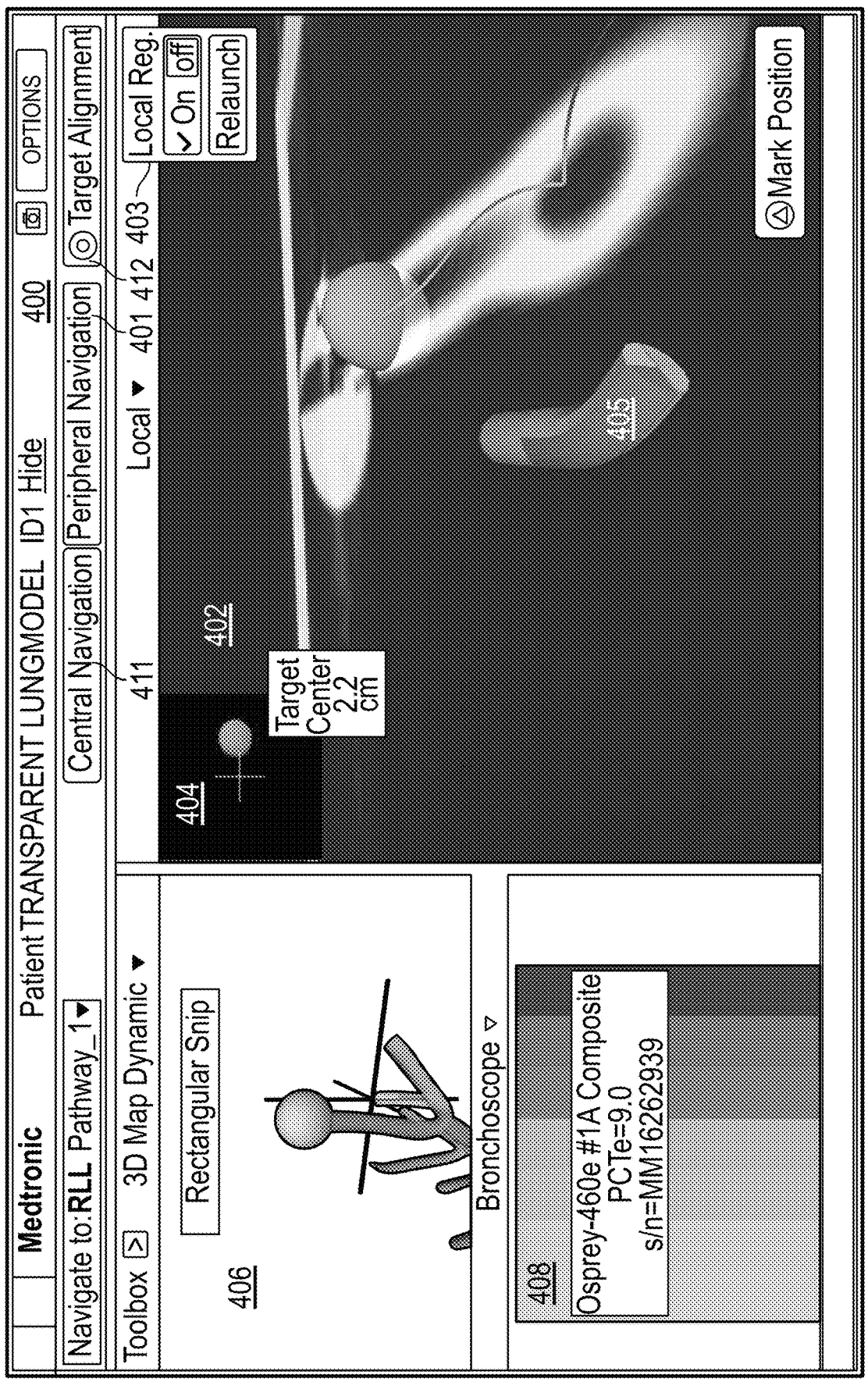
FIG. 4 is a screen shot of an example navigation user interface without a target overlay feature in accordance with the disclosure.

When the clinician selects button 306, the peripheral navigation screen associated with the "Peripheral Navigation" tab 401 of the user interface 400 of FIG. 4, which was previously displayed prior to performing the local registration process, is redisplayed showing adjustments, if any, to the position and/or orientation of the navigation catheter tip 405 as a result of the location registration process. The peripheral navigation screen 401 includes a local CT view 402, a 3D navigation catheter tip view 404, a 3D map view 406, and a bronchoscope view 408. The peripheral navigation screen 401 also includes a local registration user controls 403 enabling the user to apply local registration and/or relaunch local registration. The user interface 400 also includes a "Central Navigation" tab 411 and a "Target Alignment" tab 412, which may be individually selected to perform central navigation or target alignment, respectively.

Figure 5:
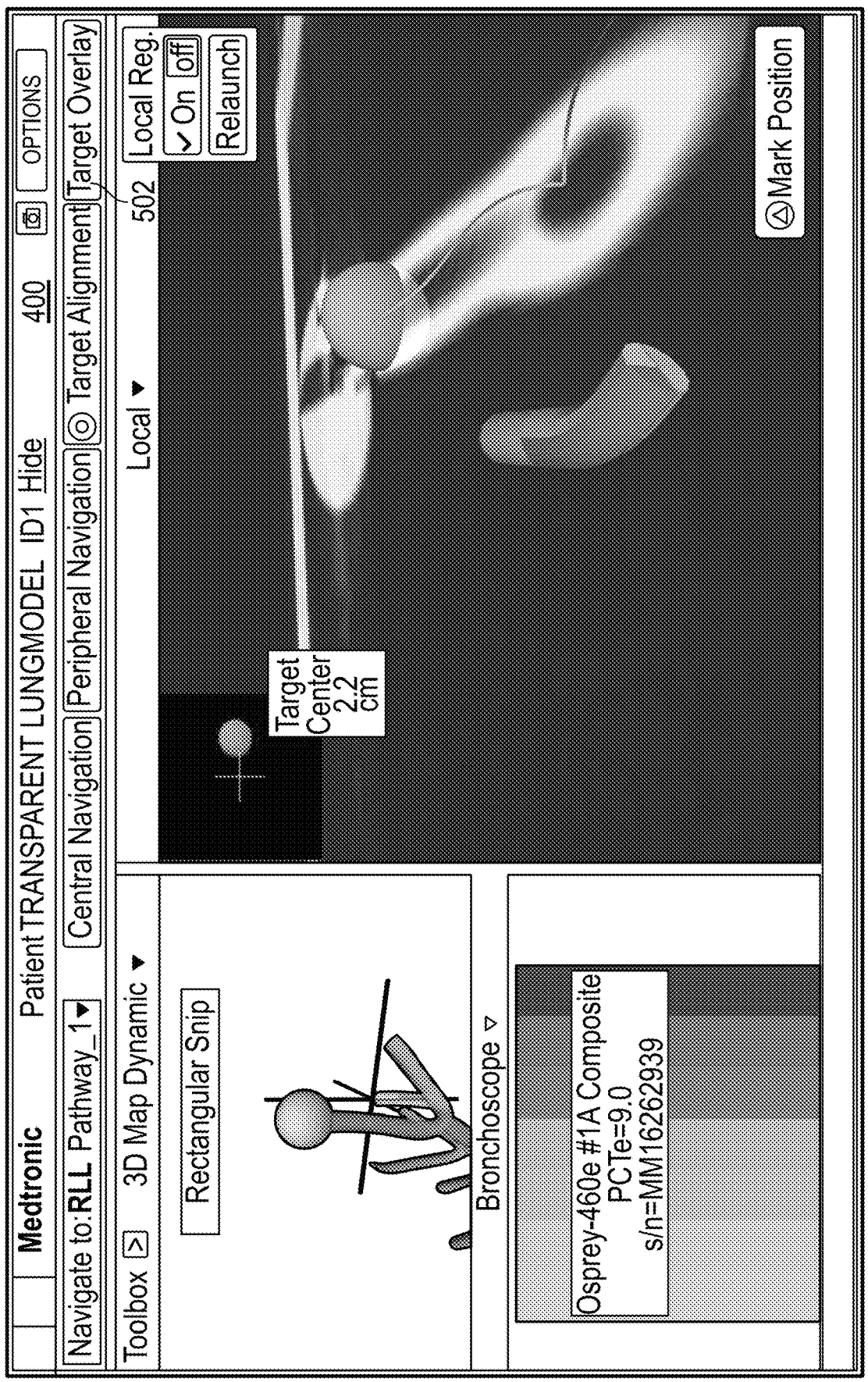
FIG. 5 is a screen shot of an example navigation user interface with the target overlay feature in accordance with the disclosure.
Figure 6:
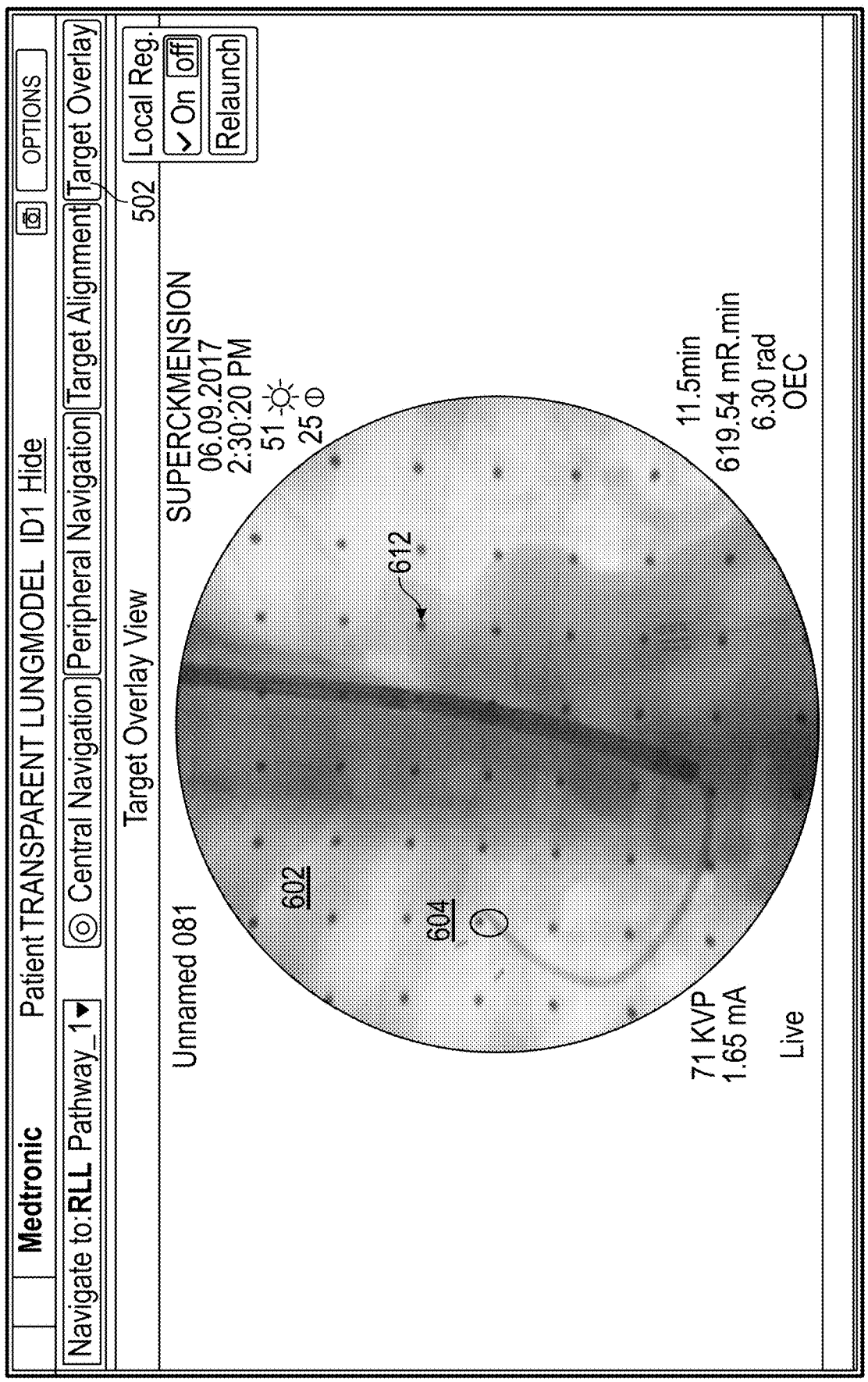
FIG. 6 is a screen shot of an example navigation user interface illustrating a screen that appears when a "Target Overlay" tab is selected in accordance with the disclosure.

When the clinician selects button 403, the user interface 400 displays the peripheral navigation screen and a "Target Overlay" tab 502 illustrated in FIG. 5. When the target overlay tab 502 is selected, a target overly screen is displayed as seen in FIG. 6 which includes a live fluoroscopic view 602 of the catheter 102 in the patient "P".

Figure 7:
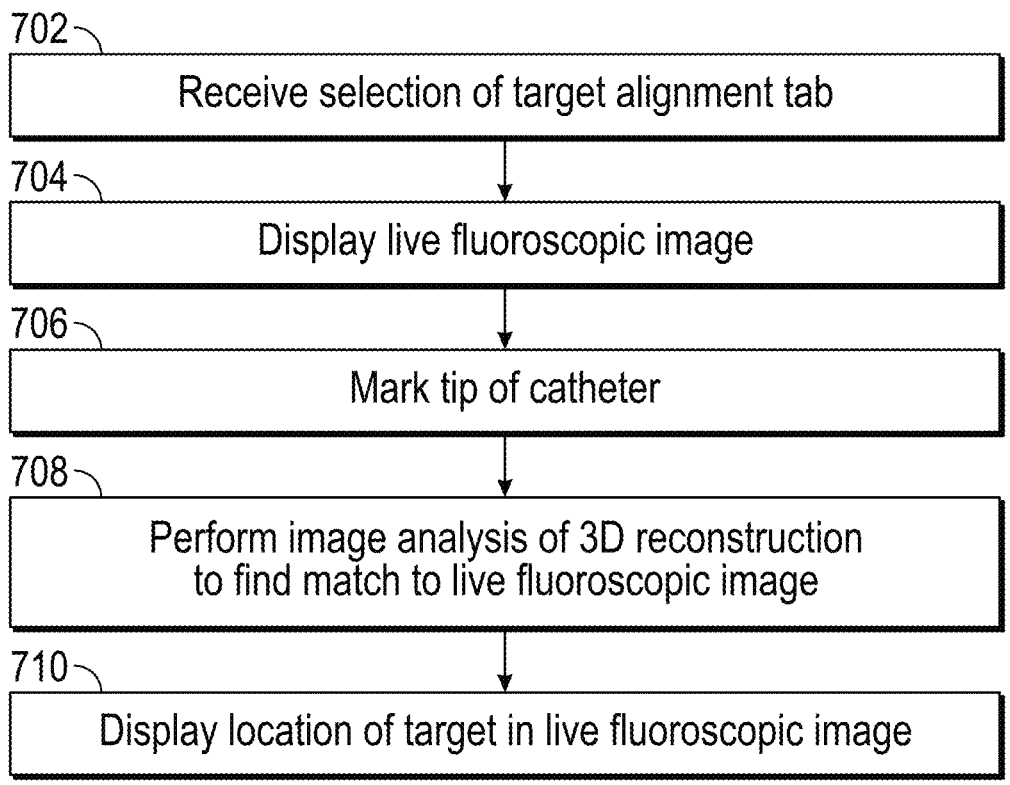
FIG. 7 is a flow diagram of an example method presenting a target on a live fluoroscopic image in accordance with the disclosure.

As illustrated in FIG. 7, following selection of the target alignment tab 502 at step 702, a live fluoroscopic image 602 (FIG. 6) is displayed at step 704. Once the live fluoroscopic image 602 is displayed, the computing device 122 may request marking of the position of the tip 604 of catheter 102 in the fluoroscopic image at step 706. As an alternative, the marking of the tip 602 may be automatically performed by an image analysis application and may optionally be presented to a user to simply confirm. For example, this may be based on identifying all the pixels in the image that have above a certain threshold Hounsfield unit value, which will be the radio opaque catheter. The last connected pixel of the pixels making up the catheter 102 will be the tip 602 of the catheter 102. Of course, other processes may also be used for catheter 102 tip 602 detection without departing from the scope of the disclosure.

At step 708, following receipt of the position of the tip 604 of the catheter in the fluoroscopic image 602, the computing device performs an image analysis of the live fluoroscopic image 602, and the fluoroscopic 3D reconstruction acquired during the local registration process. The image processing at step 708 compares the live 2D fluoroscopic image 602 to slices of the fluoroscopic 3D reconstruction to determine a best match. This best match may be based on the shape of the catheter 102 in each of the slices of the fluoroscopic 3D reconstruction as compared to the shape of the catheter 102 in the live fluoroscopic image. Additionally or alternatively, the best match may be based on the marked position of the tip 604 of the catheter 102 in the live fluoroscopic image 602, and that marked during the local registration process. Still further, the computing device 122 may compare the detected position of the catheter 102 by the tracking system 114 immediately following the local registration to the current detected position of the catheter 102. Any of these techniques may also be used in combination to assist in the matching. Although generally described as comparing the live 2D fluoroscopic image 602 to slices of the fluoroscopic 3D reconstruction to determine a best match, it is contemplated that any suitable means of identifying a best match of the live fluoroscopic image 602 to images captured during local registration may be utilized. In embodiments, the position of the fluoroscopic imaging device 124 relative to the grid of radio opaque markers 612 adjacent the transmitter mat 120 may be identified and the location of the tip 604 of the catheter 102 can be utilized to identify the location of the fluoroscopic imagine device 124 in the same dimensional space as the tip 604 of the catheter 102 (e.g., the same coordinate system).

Figure 8:
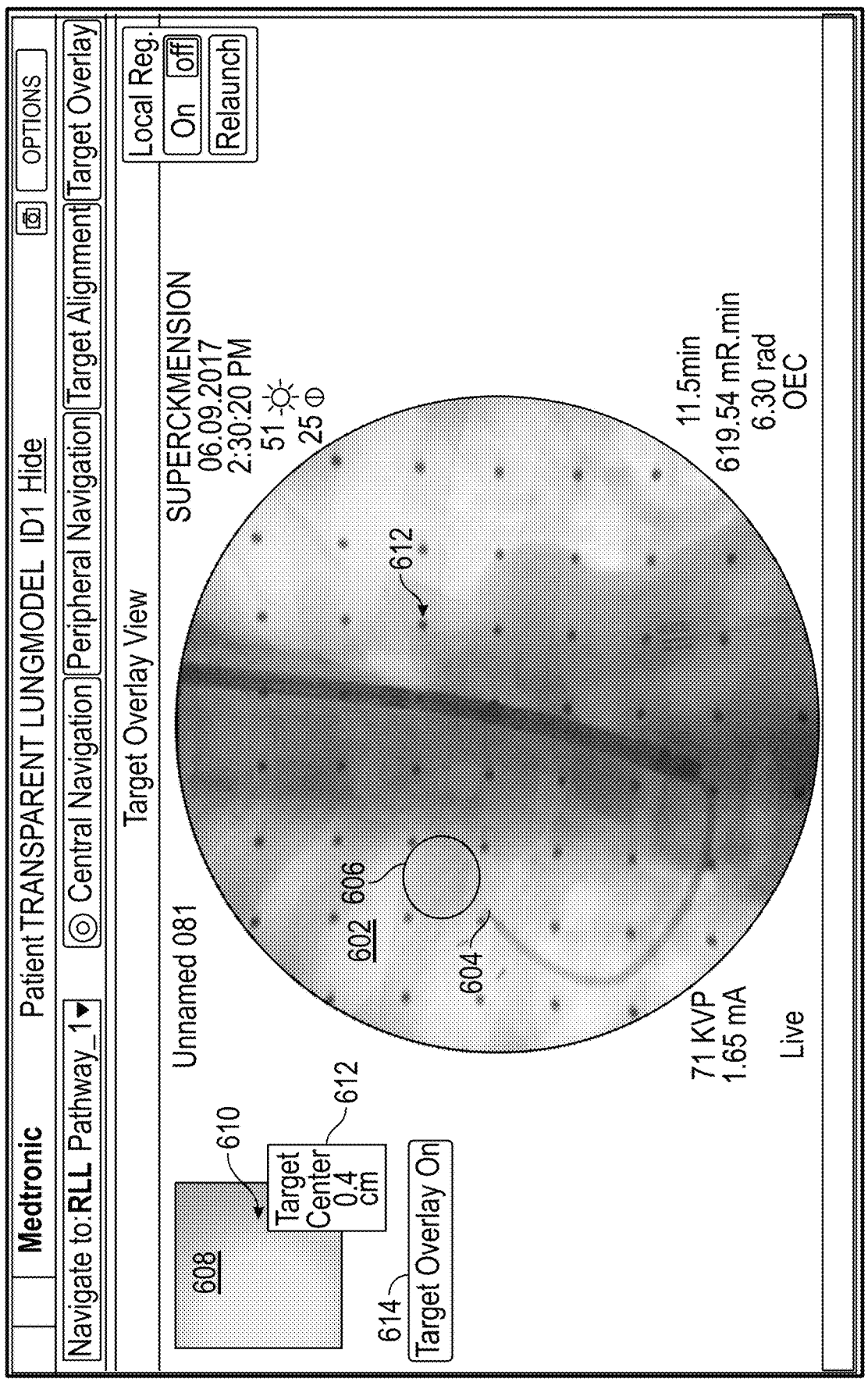
FIG. 8 is a screen shot of an example navigation user interface showing a target marker overlaid on a real-time two-dimensional (2D) fluoroscopic view in accordance with the disclosure.

Following the image analysis, the computing device displays a location of the target, whose position relative to the catheter 102 was determined during the local registration and displays a target marker 606 on the live fluoroscopic image 602 at step 710 as depicted in FIG. 8. This position of the target marker 606 is based on the location of the target that was marked during the local registration process employing the fluoroscopic 3D reconstruction.

In the example of FIG. 8, the tip 604 of the catheter 102 is shown as aligned with the target marker 606 which is displayed in the live fluoroscopic view 602. In addition, a medical device tip view 608 depicts the view as if a camera were located at the tip 604 of the catheter 102. The medical device tip view 608 presents a three-dimensional representation 610 of the target 606. If the tip 604 of the catheter 102 is nearly aligned with the target, the target marker 606 may be displayed in a first color (e.g., green) and overlaid on the live fluoroscopic view 602. If, on the other hand, the tip 604 of the catheter 102 were not aligned with the target (for example, as shown in the 3D navigation catheter tip view 404 of FIG. 4 in which the spherical target is disposed to the right of the center of the 3D navigation catheter tip view 404), the target marker 606 may be displayed in a different color, e.g., orange or red. Similarly, in the medical device tip view 608 where the tip 604 of the catheter 102 is not aligned with the target, the 3D representation 610 of the target 606 will appear offset in the image, and only a portion or none of it may be visible in that view. In addition, the color may also change as described above depending on the severity of the misalignment of the tip 604 of the catheter 102 and the target The medical device tip view 608 may also include a text box 612, which displays text indicating a distance between the tip 604 of the catheter 102 and the center of target. In embodiments, the computing device 122 may calculate the distance by aligning or finding the correspondence between the 3D model of the luminal network, which may be based on a CT scan and which includes the target, and the live fluoroscopic view, and measuring the distance between the tip 604 and the center of the 3D model of the target using, for example, image processing. In finding the correspondence between the 3D model and the live fluoroscopic view, the fluoroscopic 3D reconstruction generated and marked in the local registration process may be used. In embodiments, the distance is measured from a center of or an outside edge of the target. The target overlay screen further includes a target overlay toggle button 614, which, when selected, toggles between displaying the target marker 606 as shown in FIG. 8 and not displaying the target marker 606.

Figure 9:
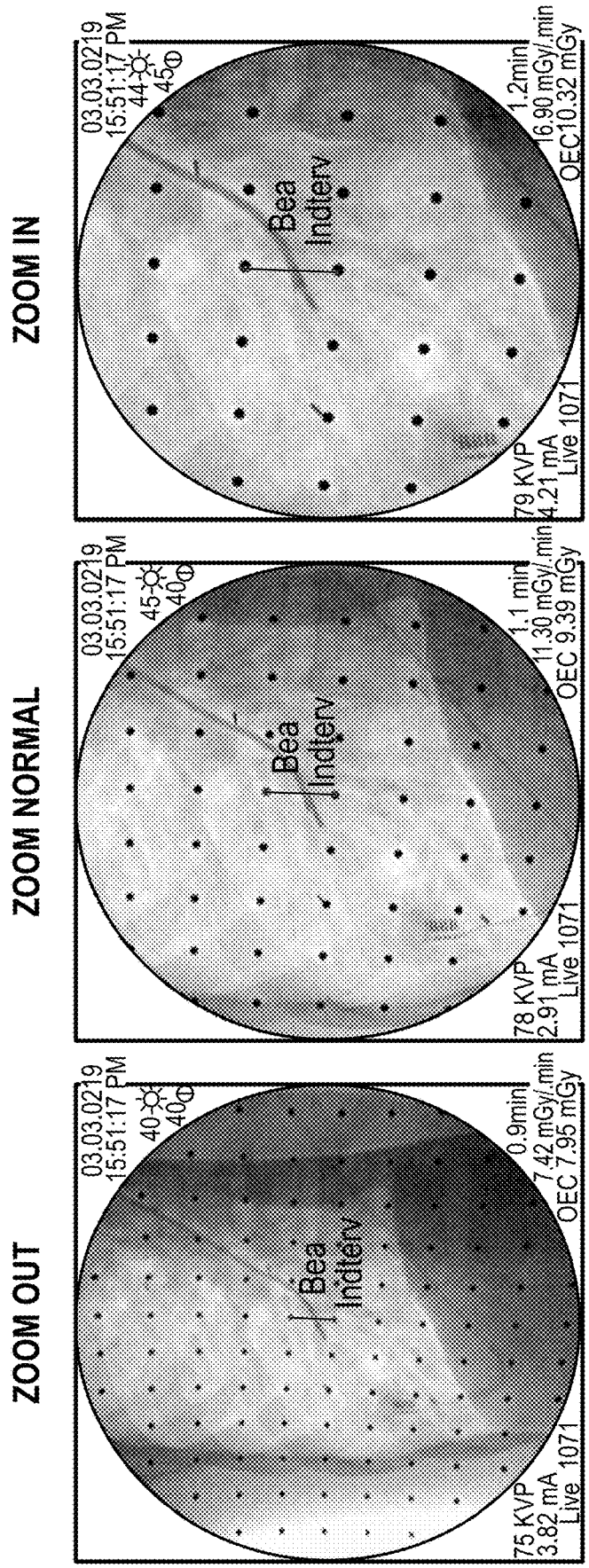
FIG. 9 depicts three fluoroscopic images at different levels of zoom.

While FIG. 7 depicts the general overview of a target overlay method and the result of the target overlay. While effective, the capabilities of the fluoroscope and actions which occur during a procedure may require further refinements of the process. One of the challenges that can occur when using a fluoroscope and comparing or importing aspects from one set of images to another is determining the level of zoom of a given image. Fluoroscopes generally have three levels of zoom. As depicted in FIG. 9, one level is zoom out (e.g., no zoom), a second is normal, and the third is zoom in. During a procedure, it is not uncommon for a clinician to perform the local registration, described above, at one level of zoom, for example zoom out, and then when seeking to perform the biopsy move the fluoroscope to a normal or zoom in level to provide greater clarity of the procedure in the live images. In FIG. 9 the difference in zoom level can be observed by comparing the interval between the radio opaque markers 612 at each level of zoom. The catheter 102 is easily observable in each image of FIG. 9, however, as will be appreciated, by changing the level of zoom, an overlaid position of a target captured at a normal level of zoom might be overlaid in an entirely improper position if the level of zoom for the live fluoroscopic images is changed to zoom out or zoom in levels.

Figure 10:
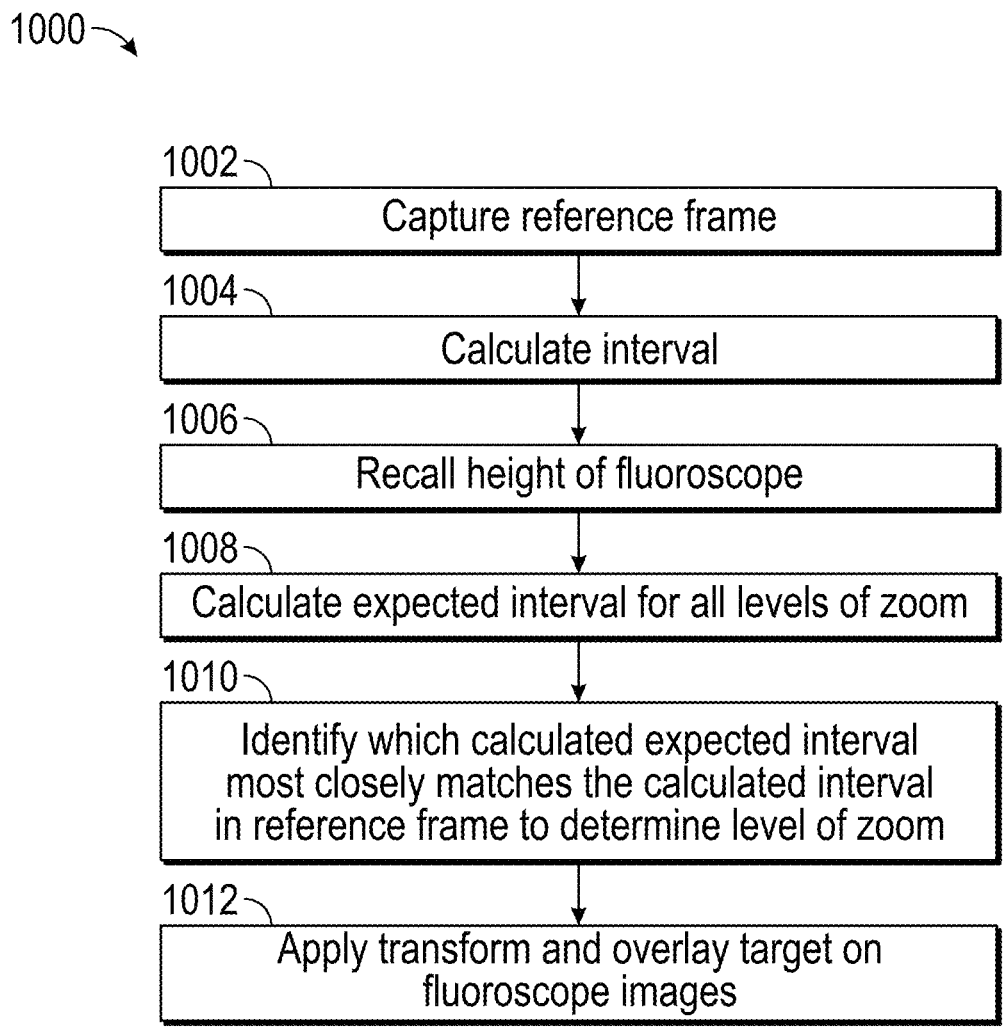
FIG. 10 is a flow diagram for determining the level of zoom as depicted in FIG. 9.

FIG. 10 is a flow chart that the computing device 122 may undertake to determine the level of zoom of the fluoroscope. At step 1002 a reference frame is captured by the fluoroscope 124. The reference frame is a live fluoroscopic image. At step 1004 the distance or interval between two radio opaque markers 612 is calculated. In one example, the interval is calculated between two for a center column of radio opaque markers 612. At step 1006 the, the height of the fluoroscope 124 from the transmitter mat 120 on which the radio opaque markers 612 are incorporated, which was determined as part of the local registration is recalled from memory within the computing device 122. The height of the fluoroscope 124 is determined while at a zoom-out configuration. As can be appreciated, the height of the fluoroscope 124 relative to the transmitter mat 120 may have a similar effect as increasing or decreasing the level of zoom. Therefore, it is contemplated that the height of the fluoroscope 124 is maintained during the procedure to ensure that the level of zoom is not altered by a fluctuation of the height of the fluoroscope 124. At step 1008 a simulation is performed to calculate an expected interval between the radio opaque markers 612 at the height and angle of the fluoroscope 124 at which the reference frame was captured for all possible zoom options. At step 1010 the zoom level in which the calculated interval between the radio opaque markers 612 most closely matches the determined interval of the radio opaque markers 612 in the reference frame is identified as the zoom level of the reference frame. With the zoom level of the reference frame determined the computing device can apply a transform at step 1012 such that the location of the target, identified during the local registration can be accurately overlaid on the live fluoroscopic image. In one non-limiting embodiment, the zoom level may be calculated using the known height of the fluoroscope 124 and the calculated interval between radio opaque markers 612. In this manner, rather than selecting the zoom level that most closely matches the calculated interval between the radio opaque markers 612, the zoom level may be estimated or a zoom level that falls between the zoom out, normal zoom, and zoom in positions may be utilized. As can be appreciated, estimating or calculating the zoom interval reduces computational time, reduces the energy required to make the computation, and may support an option where a continuous zoom level may be utilized (e.g., no discrete zoom levels but rather a fluidly changing zoom level).

It has been determined that this process can be employed when the fluoroscope 124 is in the AP position as well as at angles to the AP position without impeding its utility. The fluoroscopic sweep for local registration may be taken through about 30-60 degrees to generate the 3D volumetric reconstruction. In embodiments, the fluoroscopic sweep for local registration may be taken through a range of about 200 degrees. Zoom detection from at least about +45 to −45 degrees has been found to be equally effective regardless of the angle of the fluoroscope 124 when determining the level of zoom.

A second aspect of use of a fluoroscope 124 for acquisition of biopsies that needs to be accounted for is the issue of movement of the fluoroscope 124. In general, there are two types of movement intentional movements and unintentional movements. Most unintentional movements may be caused by a doctor or nurse inadvertently bumping the fluoroscope 124, whereas intentional movements are those that are intended by the doctor. It is these intentional movements that this instant aspect of the disclosure is intended to detect.

Figure 11:
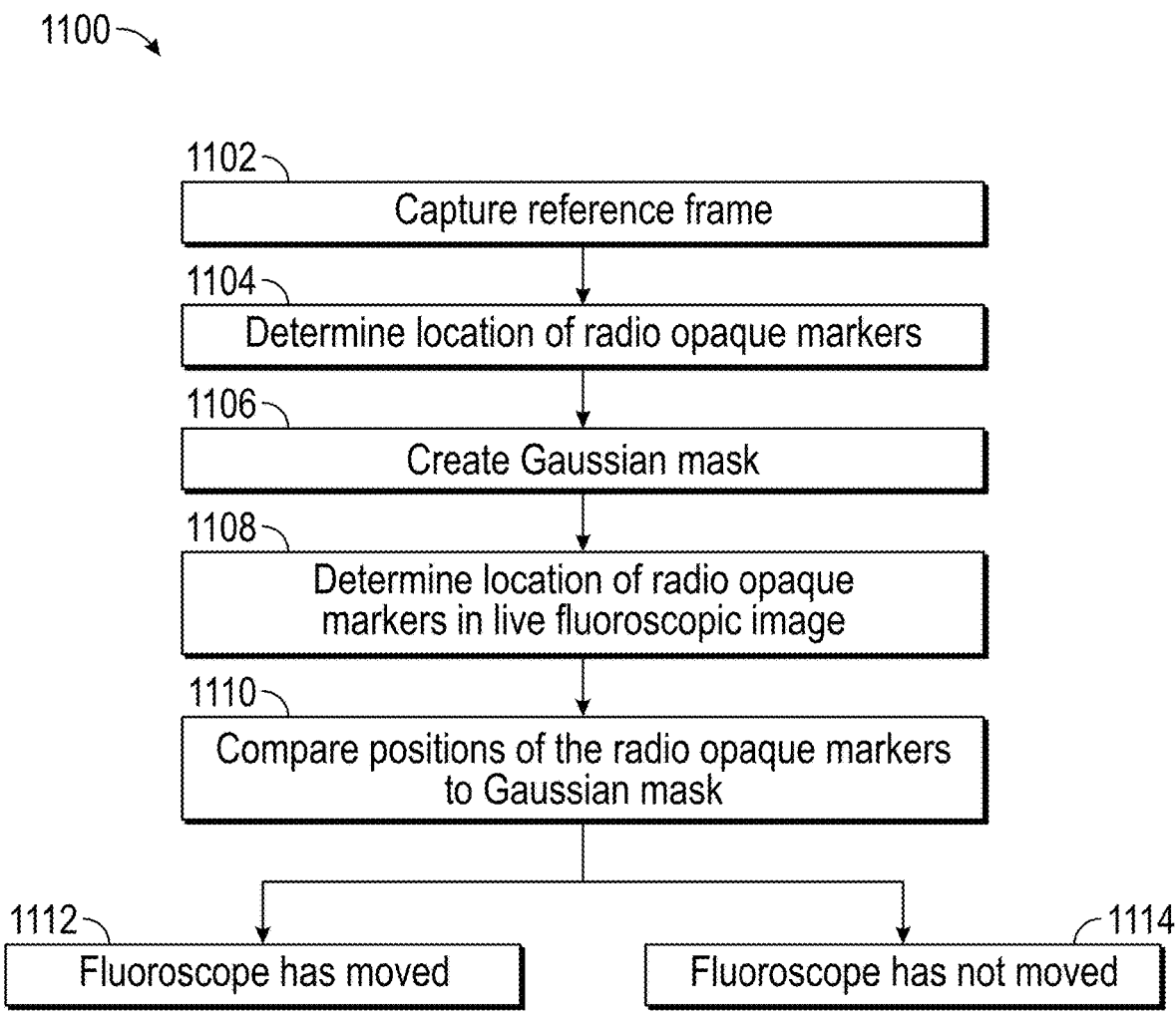
FIG. 11 is a flow diagram for determining whether a fluoroscope has moved as compared to a reference frame.

As FIG. 11 details a process 1100 for determining whether the above described intentional movements of the fluoroscope 124 have occurred. An initial step of movement detection, a reference frame is captured at step 1102. This may in fact be the same reference frame that was captured at step 1002 of the zoom detection. At step 1104 the locations of the radio opaque markers 612 in the reference frame are determined. This may be performed for example via thresholding or other image processing techniques to identify the locations of the radio opaque markers 612 in the reference frame. These determined positions of the radio opaque markers 612 are the two-dimensional positions of the radio opaque markers 612 in the fluoroscope coordinate system.

Figure 12:
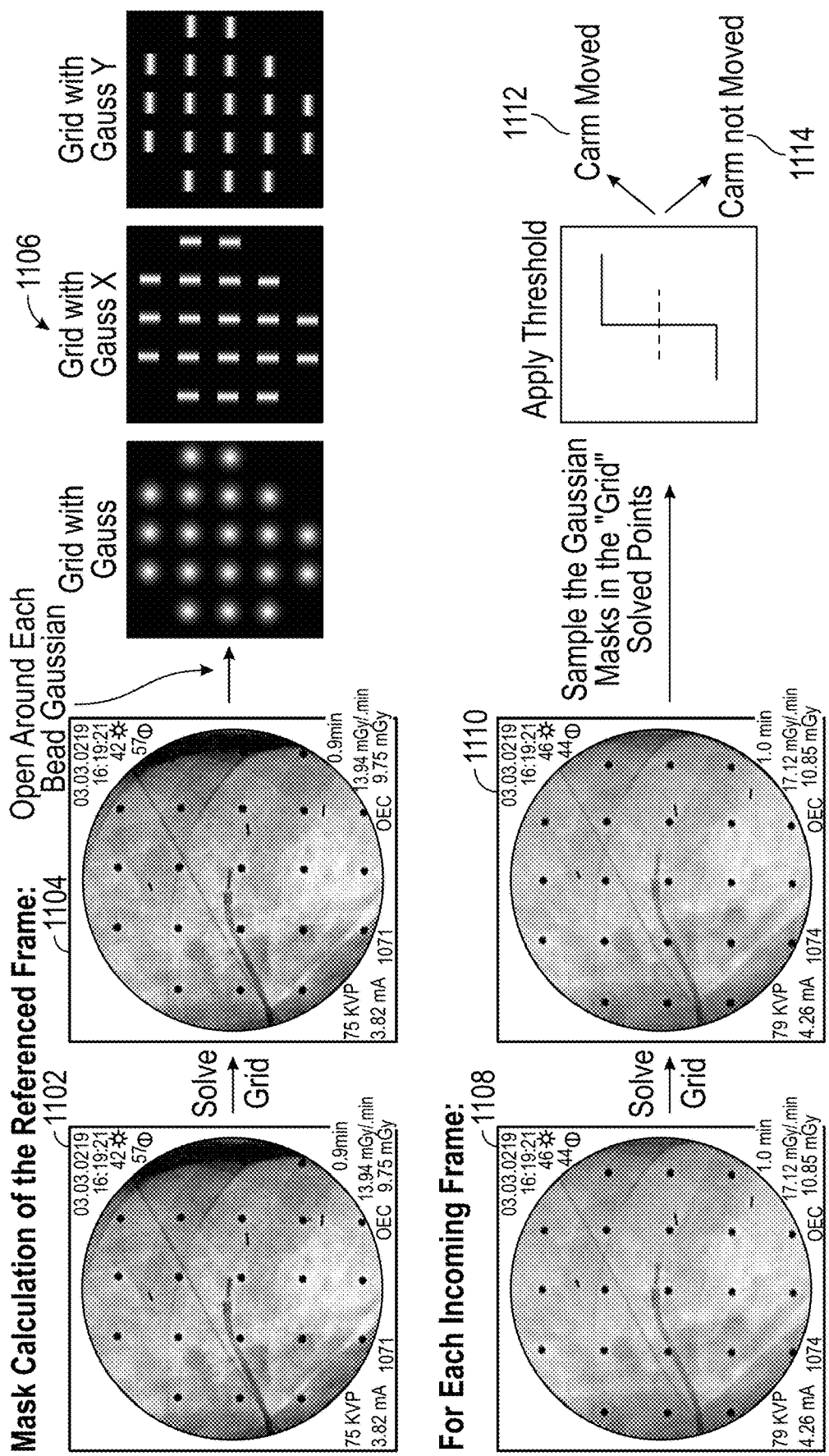
FIG. 12 is a graphical representation of the flow diagram of FIG. 11.

Once the positions of the radio-opaque markers 612 are determined, a Gaussian mask is created at step 1106. The Gaussian mask defines an acceptable range around the detected location of the radio opaque markers 612. As depicted in FIG. 12, the Gaussian mask defines an acceptable rage of movement in both the X and the Y directions. FIG. 12 graphically depicts the steps outlined in FIG. 11 thus the same reference numerals are used to depict the steps described with respect to FIG. 11 as they are shown in FIG. 12.

Once the Gaussian mask is defined at step 1106, for each live fluoroscopic image (e.g., each frame of a fluoroscopic video) acquired by the fluoroscope 124 while the clinician is seeking to perform a biopsy or other procedure, at step 1108 again the position of the radio opaque markers 612 is determined in the same manner as in the reference frame at step 1104. The position of the radio opaque markers is then compared at step 1110 to the Gaussian mask. If the position of the radio opaque markers 612 is outside of the Gaussian mask, the determination is made at step 1112 it is an indicator that for that frame or single image the fluoroscope 124 has moved. If position of the radio opaque markers 612 is inside of the Gaussian mask, the determination is made at step 1114 that for that frame or single image the fluoroscope 124 has not moved. Although generally referred to as being a Gaussian mask, it is contemplated that any suitable method of analyzing location of the radio opaque markers 612 within a fluoroscopic image may be utilized.

Figure 13:
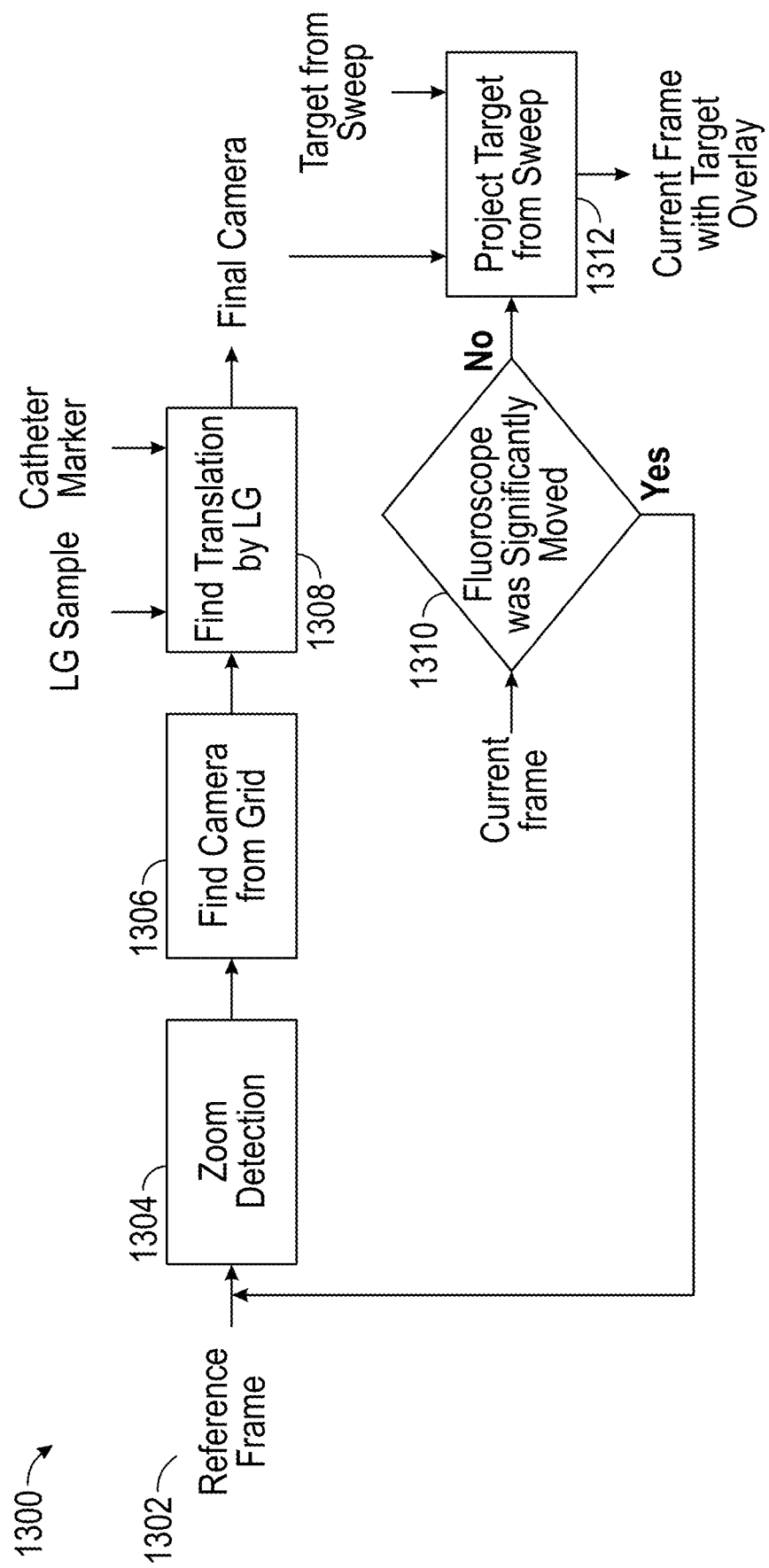
FIG. 13 is a flow diagram for a method of incorporating the methods of FIGS. 10 and 11 to enable overlay of a previously identified target in a live fluoroscopic image.

FIG. 13 depicts a work-flow 1300 incorporating the zoom determination and the movement detection principals described herein. In accordance with the work flow a reference frame is captured at step 1302. Following capture of the reference frame zoom detection is undertaken at step 1304. This zoom detection is in accordance with the procedure outlined with respect to FIG. 10. Next, at step 1306, the position of the radio opaque markers 612 in the reference image and generation of the Gaussian mask is undertaken. At step 1308 the clinician is requested to mark the distal end of the catheter 102. At the same time the computing device 122 acquires the electromagnetic position of the distal end of the catheter 102 from the sensor 104 or 126 and the computing device 122 calculates a translation or position of the fluoroscopic imaging device 124 in the navigation coordinate system (e.g., antenna coordinates). As can be appreciated, with the height of the fluoroscope 124 known, the translation may be calculated for the remaining two coordinates or positional indicators of the catheter 102 using the position of the distal end of the catheter 102. With the X, Y, and Z coordinates known, the position of the distal end of the catheter 102 can be determined. As can be appreciated, knowing the position of the fluoroscope 124 in the navigation coordinate system enables the estimated target location to be accurately projected onto the live fluoroscopic image.

Once complete, the live images from the fluoroscope 124 are analyzed by the process described in connection with FIG. 11 regarding determination of movement at step 1310. As a result, when it is determined that there has been no movement or at least no movement over the thresholds defined by the Gaussian mask, the target location of the target identified in the local registration can then be projected on the live fluoroscopic images at step 1312. If the determination is made that the fluoroscope 124 has moved an amount greater than the threshold amounts defined by the Gaussian masks from when the reference image was acquired, the entire process can revert back to step 1302 and require the acquisition of a new reference image. The determination of movement for each frame of the fluoroscopic images is stored in memory. In one embodiment, as described in greater detail below, a determination to cease target overlay of step 1312 may be made when a threshold number of images (e.g., successive images) indicate that the fluoroscope 124 has moved.

Though in its simplest from a single image determined at step 1310 to represent that the fluoroscope 124 has moved could result in cessation of the process and require acquisition of a new reference image the instant disclosure is not so limited. As will be appreciated, there are instances where the fluoroscope 124 may be bumped or disturbed by a doctor or nurse during the procedure. In such instances, because the fluoroscope may oscillate following being disturbed, each frame may not be found to depict the radio opaque markers 612 outside of the thresholds set by the Gaussian mask. Further, the oscillations may become smaller and eventually cease after period of time. In such situations, where ultimately the fluoroscope 124 has not been intentionally moved, there is no need to have the process revert to step 1302.

Similarly, there are instances where a doctor or nurse may adjust the contrast or brightness of the fluoroscope 124. The result is that for a given number of frames the radio opaque markers may not be identifiable. These frames do not indicate that there was intentional movement of the fluoroscope 124, but rather some other basis for the inability to determine that the radio opaque markers are within the Gaussian mask. Again, after a period of time, or a number of frames, the radio opaque markers 612 will again be viewable, and the position of the fluoroscope relative to its position when the reference frame was acquired can be confirmed as unchanged.

In contrast, when a clinician has intentionally moved the fluoroscope 124 from the position at which the reference frame was acquired, each frame captured by the fluoroscope will have the positions of radio opaque markers fall outside of the Gaussian mask. Once sufficient frames are determined to be outside of the mask target overlay of step 1312 can be ceased and the process returns to step 1302.

Figure 14:
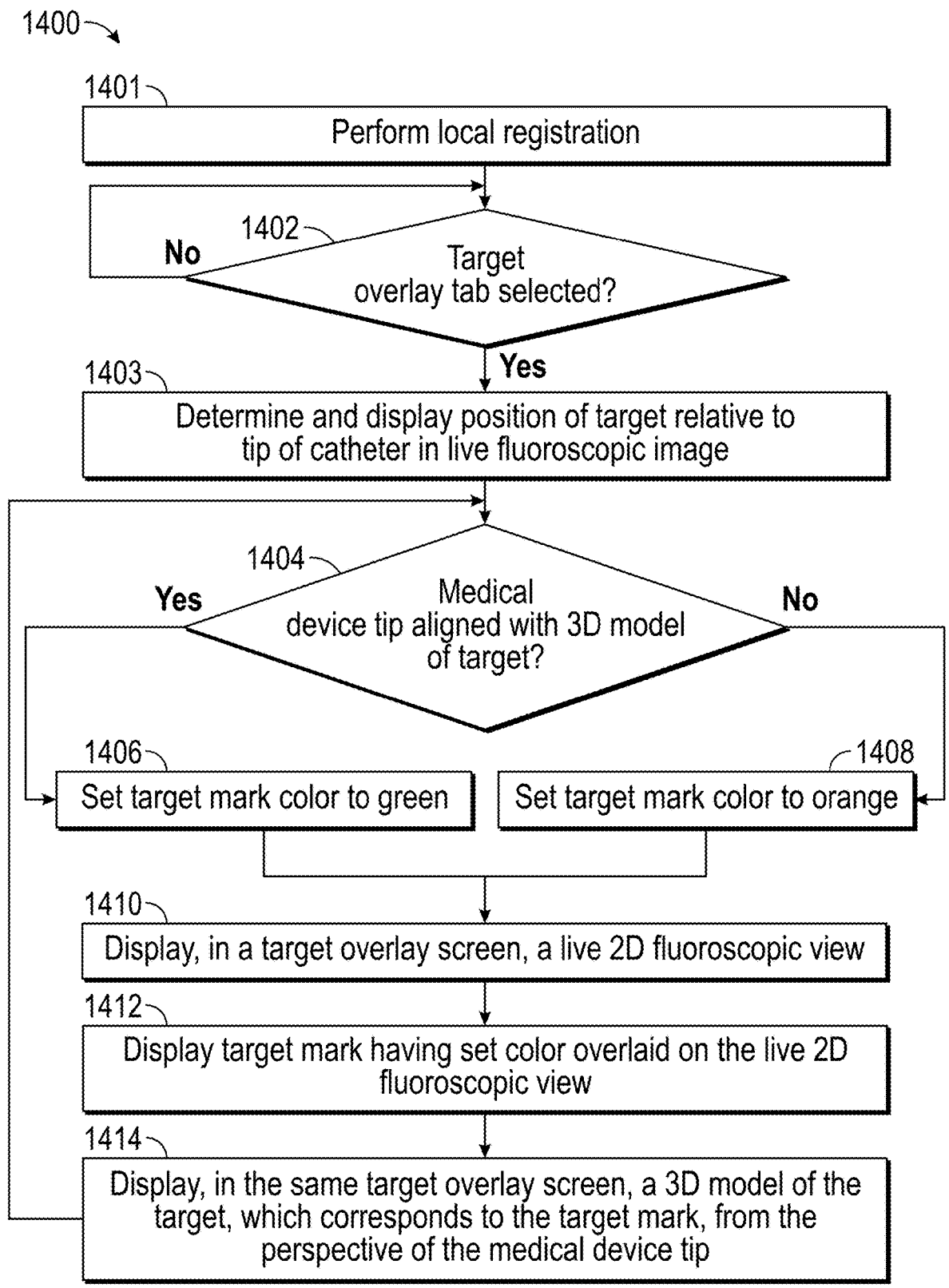
FIG. 14 is a flow diagram of an example method of visualizing the navigation of a medical device relative to a target.

FIG. 14 is a flow diagram of an example method 1400 of visualizing the navigation of the medical device tip towards a target after the medical device tip is brought into the vicinity of the target. At block 1401, following navigation proximate the target, a local registration process is performed to update and the target position in the navigation plan. Following local registration, at block 1402, the computing device 122 determines whether the "Target Overlay" tab 502 has been selected. When the "Target Overlay" tab 502 is selected, the computing device 122 determines at block 1403 the relative position of a tip 602 of catheter 102 in a live fluoroscopic image and a target which was identified during the local registration process and displays the target at the relative position in the live fluoroscopic image. This process is performed for example using the steps described above with respect to FIG. 7.

Next, the computing device determines whether the medical device tip is aligned with the target at block 1404. The computing device 122 may determine whether the medical device tip is aligned with the target by aligning or finding the correspondence between the 3D model of the luminal network, which may be based on a CT scan and which includes the target, and the live fluoroscopic view; and determining whether the medical device tip is aligned with the 3D model of the target based on the determined alignment or correspondence and applying, for example, image processing. In aligning or finding the correspondence between the 3D model and the live fluoroscopic view, the fluoroscopic 3D reconstruction generated and marked in the local registration process may be used.

When the computing device 122 determines that the medical device tip is aligned with the target, the computing device 122 sets the target mark color to green at block 1406; otherwise, the computing device 122 sets the target mark color to orange at block 1408. At block 1410, the computing device 122 displays, in a target overlay screen, a live 2D fluoroscopic view, which at least shows the medical device. At block 1412, the computing device 122 displays a target mark having the set color overlaid on the live 2D fluoroscopic view. At block 1414, the computing device 122 displays, in the same target overlay screen, a 3D virtual target, which corresponds to the target mark, from the perspective of the medical device tip. Blocks 1404-1414 may be repeated until the medical device tip is placed at the center of the target or until the biopsy or other treatment is completed. This final navigation allows the user to use fluoroscopic navigation techniques to obtain live images with the target marked on the live images, which enables the user to see how well the medical device tip is aligned with the target to ensure that the medical device tip reaches the target to take a sample of the target or perform treatment on the target.

In a further aspect of the disclosure, following the local registration (e.g., step 901) the computing device 122 may undertake an image analysis of the fluoroscopic 3D reconstruction to determine an angle for placement of the fluoroscopic imaging device 124 to optimally engage in the target overlay tab. In this aspect of the disclosure, following the identification of the tip of the catheter 102 in two slices of the fluoroscopic 3D reconstruction, and identification of the target in the fluoroscopic 3D reconstruction and determining the relative position of the tip of the catheter 102 and the target in the fluoroscopic 3D reconstruction, the computing device performs an image analysis of the 3D reconstruction to determine a slice of the 3D reconstruction at which the catheter and the target visible. This may be the slice where both the target and the catheter 102 are most visible or most visible beyond some minimum threshold. Those of skill in the art will appreciate that there will be slices in which one or the other (or both) of the catheter or target are not visible and those images will likely be ignored by the computing device 122 when performing this analysis.

After analyzing the remaining slices of the fluoroscopic 3D reconstruction, one of the slices is identified as most clearly depicting both the catheter 102 and the target. Once the slice of the 3D reconstruction is determined, the position (e.g., angle to the patient P or operating table 112) of the fluoroscopic imaging device 124 where a corresponding 2D fluoroscopic image, such as image 602, can be captured. This position of the fluoroscopic imaging device 124 can be presented to the clinician on a user interface prior to engaging the "Target Overlay" tab 502, so that they can manually move the fluoroscopic imaging device 124 to that position. Alternatively, the fluoroscopic imaging device 124 may receive an indication of the position determined by the computing device 122 and automatically drive the fluoroscopic imaging device to that position such that upon selecting the "Target Overlay" tab 502 the fluoroscopic image 602 is acquired at this pre-determined optimum position for viewing the catheter 102 and target.

Another aspect of the disclosure is the enablement of the use of zoom features which may be built into the fluoroscopic imaging device 124. As depicted in FIG. 6, the live 2D fluoroscopic image 602 includes a plurality of radio opaque markers 612. These radio opaque markers 612 may be placed on or embedded in the transmitter mat 120. The distances between the radio opaque markers is fixed and known by the computing device 122. Because the distances between the radio opaque markers 612 is known, if the distance between any of the markers exceeds the known distances the computing device 122 can determine that the zoom features of the fluoroscopic imaging device 124 are engaged. The exact amount of zoom that has been engaged can be determined by comparing the spacing of radio opaque markers 612 in the 2D fluoroscopic image 602 to the known spacing of the radio opaque markers 612 in the transmitter mat 120. Once the amount of zoom is determined, the computing device can calculate an offset in the relative position of the tip 604 of the catheter 102 and the target such that the target marker 606 can be accurately displayed in the fluoroscopic image 602 despite the change in zoom from when the local registration process was undertaken.

Figure 15:
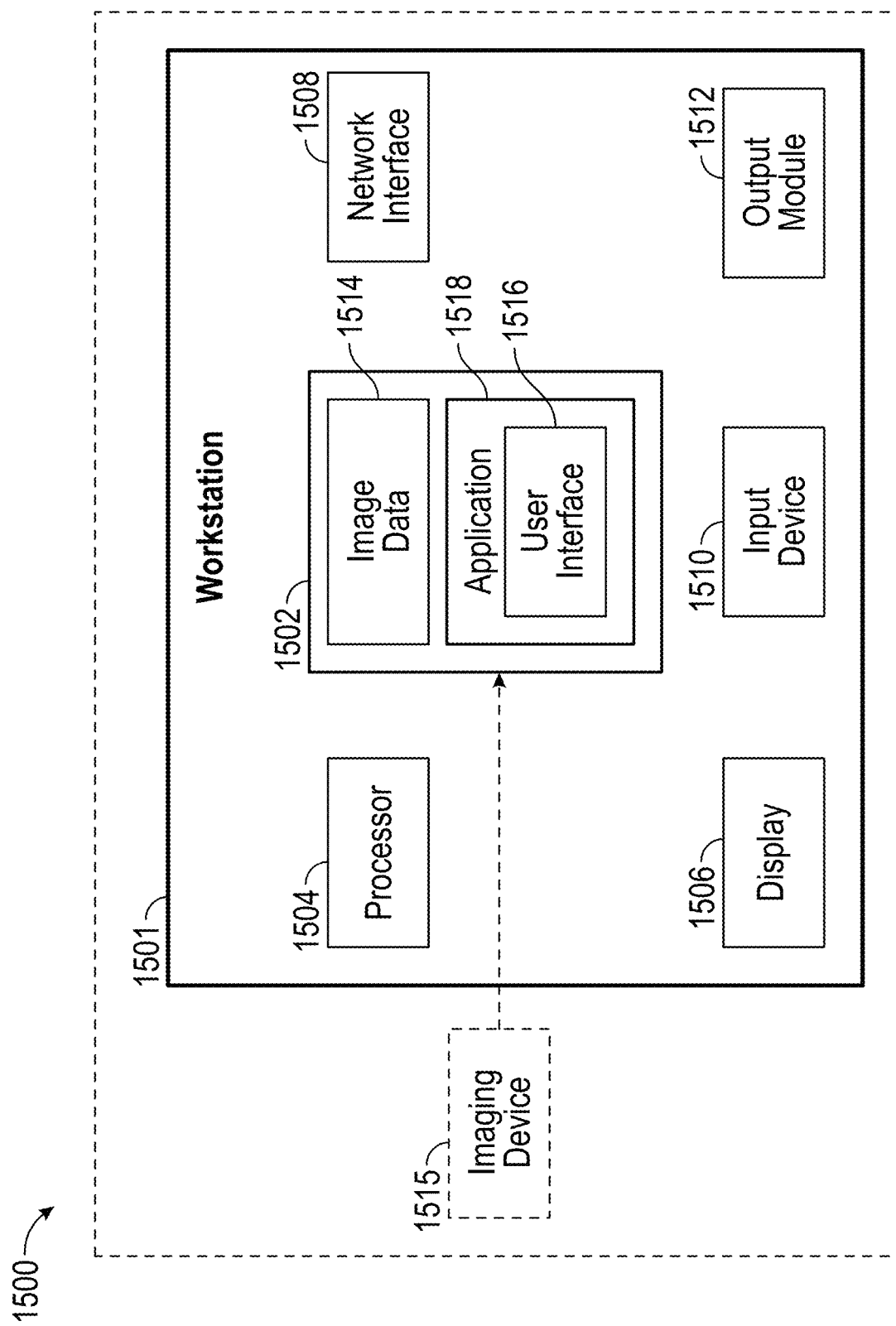
FIG. 15 is a schematic diagram of a system in accordance with the disclosure for navigating to a target and displaying user interfaces in accordance with the disclosure.

Reference is now made to FIG. 15, which is a schematic diagram of a system 1000 configured for use with the methods of the disclosure including the method of FIG. 14. System 1500 may include a workstation 1501, and optionally a fluoroscopic imaging device or fluoroscope 1515. In some embodiments, workstation 1501 may be coupled with fluoroscope 1515, directly or indirectly, e.g., by wireless communication. Workstation 1501 may include a memory 1502, a processor 1504, a display 1506 and an input device

1510. Processor or hardware processor 1504 may include one or more hardware processors. Workstation 1501 may optionally include an output module 1512 and a network interface 1008. Memory 1502 may store an application 1518 and image data 1514. Application 1518 may include instructions executable by processor 1504 for executing the methods of the disclosure including the method of FIGS. 10, 11, 13 and 14.

Application 1518 may further include a user interface 1516. Image data 1514 may include the CT scans, the generated fluoroscopic 3D reconstructions of the target area and/or any other fluoroscopic image data and/or the generated one or more slices of the 3D reconstruction. Processor 1504 may be coupled with memory 1502, display 1506, input device 1510, output module 1512, network interface 1508 and fluoroscope 1515. Workstation 1501 may be a stationary computing device, such as a personal computer, or a portable computing device such as a tablet computer. Workstation 1501 may embed a plurality of computer devices.

Memory 1502 may include any non-transitory computer-readable storage media for storing data and/or software including instructions that are executable by processor 1504 and which control the operation of workstation 1501 and, in some embodiments, may also control the operation of fluoroscope 1515. Fluoroscope 1515 may be used to capture a sequence of fluoroscopic images based on which the fluoroscopic 3D reconstruction is generated and to capture a live 2D fluoroscopic view according to this disclosure. In an embodiment, memory 1502 may include one or more storage devices such as solid-state storage devices, e.g., flash memory chips. Alternatively, or in addition to the one or more solid-state storage devices, memory 1502 may include one or more mass storage devices connected to the processor 1504 through a mass storage controller (not shown) and a communications bus (not shown).

Although the description of computer-readable media contained herein refers to solid-state storage, it should be appreciated by those skilled in the art that computer-readable storage media can be any available media that can be accessed by the processor 1504. That is, computer readable storage media may include non-transitory, volatile and non-volatile, removable and non-removable media implemented in any method or technology for storage of information such as computer-readable instructions, data structures, program modules or other data. For example, computer-readable storage media may include RAM, ROM, EPROM, EEPROM, flash memory or other solid-state memory technology, CD-ROM, DVD, Blu-Ray or other optical storage, magnetic cassettes, magnetic tape, magnetic disk storage or other magnetic storage devices, or any other medium which may be used to store the desired information, and which may be accessed by workstation 1501.

Application 1518 may, when executed by processor 1504, cause display 1506 to present user interface 1516. User interface 1516 may be configured to present to the user a single screen including a three-dimensional (3D) view of a 3D model of a target from the perspective of a tip of a medical device, a live two-dimensional (2D) fluoroscopic view showing the medical device, and a target mark, which corresponds to the 3D model of the target, overlaid on the live 2D fluoroscopic view, as shown, for example, in FIG. 8. User interface 1516 may be further configured to display the target mark in different colors depending on whether the medical device tip is aligned with the target in three dimensions.

Network interface 1508 may be configured to connect to a network such as a local area network (LAN) consisting of a wired network and/or a wireless network, a wide area network (WAN), a wireless mobile network, a Bluetooth network, and/or the Internet. Network interface 1508 may be used to connect between workstation 1501 and fluoroscope 1515. Network interface 1508 may be also used to receive image data 1514. Input device 1510 may be any device by which a user may interact with workstation 1501, such as, for example, a mouse, keyboard, foot pedal, touch screen, and/or voice interface. Output module 1512 may include any connectivity port or bus, such as, for example, parallel ports, serial ports, universal serial busses (USB), or any other similar connectivity port known to those skilled in the art. From the foregoing and with reference to the various figures, those skilled in the art will appreciate that certain modifications can be made to the disclosure without departing from the scope of the disclosure.

While detailed embodiments are disclosed herein, the disclosed embodiments are merely examples of the disclosure, which may be embodied in various forms and aspects. For example, embodiments of an electromagnetic navigation system, which incorporates the target overlay systems and methods, are disclosed herein; however, the target overlay systems and methods may be applied to other navigation or tracking systems or methods known to those skilled in the art. Therefore, specific structural and functional details disclosed herein are not to be interpreted as limiting, but merely as a basis for the claims and as a representative basis for teaching one skilled in the art to variously employ the disclosure in virtually any appropriately detailed structure.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of embodiments. Those skilled in the art will envision other modifications within the scope and spirit of the claims appended hereto.

What is claimed is:

1. A method of determining a level of zoom in a fluoroscopic image, comprising:
   capturing a fluoroscopic reference frame;
   calculating an interval between radio opaque markers in the reference frame;
   calculating an expected interval between the radio opaque markers for a plurality of levels of zoom;
   identifying the expected interval that most closely matches the calculated interval in the reference frame;
   applying a transform based on the identified expected interval; and
   overlaying a location of a target on a live fluoroscopic image based on a result of applying the transform.

2. The method according to claim 1, further comprising storing a height of a fluoroscope from which the fluoroscopic reference frame is captured compared to a location of the radio opaque markers.

3. The method according to claim 2, further comprising storing a height of a fluoroscope from which the fluoroscopic reference frame is captured compared to a location of the radio opaque markers.

4. The method according to claim 3, wherein calculating the expected interval between the radio opaque markers includes calculating the expected interval between the radio opaque markers at the stored height of the fluoroscope at which the reference frame was captured.

5. The method according to claim 3, wherein calculating the expected interval between the radio opaque markers includes calculating the expected interval between the radio opaque markers at the stored height and angle of the fluoroscope at which the reference frame was captured.

6. The method according to claim 1, wherein capturing the fluoroscopic reference frame includes capturing the fluoroscopic reference frame when a fluoroscope from which the fluoroscopic reference frame is captured is in an anteroposterior position.

7. The method according to claim 1, wherein capturing the fluoroscopic reference frame includes capturing the fluoroscopic reference frame through a sweep through about 30-60 degrees relative to an anteroposterior position.

8. A system for detecting movement of a fluoroscope, comprising:
- a fluoroscopic imaging device;
- a plurality of radio opaque markers disposed in a reference frame of the fluoroscope;
- a workstation in operative communication with the fluoroscope, the workstation including a memory and at least one processor, the memory storing instructions, which when executed by the processor, is configured to:
- capture a fluoroscopic reference frame;
- calculate an interval between the radio opaque markers in the reference frame;
- calculate an expected interval between the radio opaque markers for a plurality of levels of zoom;
- identify the expected interval that most closely matches the calculated interval in the reference frame;
- apply a transform based on the identified expected interval; and
- overlay a location of a target on a live fluoroscopic image based on a result of applying the transform.

9. The system according to claim 8, wherein the workstation is further configured to store a height of the fluoroscope from which the fluoroscopic reference frame is captured compared to a location of the radio opaque markers.

10. The system according to claim 9, wherein the workstation is configured to calculate the expected interval between the radio opaque markers at the stored height of the fluoroscope at which the reference frame is captured.

11. The system according to claim 8, wherein the workstation is configured to capture the fluoroscopic reference frame when the fluoroscope is in an anteroposterior position.

12. The system according to claim 8, wherein the workstation is configured to capture the fluoroscopic reference frame through a sweep through about 30-60 degrees relative to an anteroposterior position.

* * * * *